United States Patent
Ley et al.

(10) Patent No.: US 6,395,020 B1
(45) Date of Patent: *May 28, 2002

(54) STENT CELL CONFIGURATIONS

(75) Inventors: Timothy J. Ley, Shoreview; Graig L. Kveen, Maple Grove; Burns P. Doran, Albertville, all of MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/261,687

(22) Filed: Mar. 3, 1999

Related U.S. Application Data

(63) Continuation-in-part of application No. 09/036,665, filed on Mar. 4, 1998, now abandoned.

(51) Int. Cl.$^7$ ................................................ A61F 2/06
(52) U.S. Cl. .................................................... 623/1.15
(58) Field of Search ............................... 623/1.11, 1.12, 623/1.13, 1.14, 1.15, 1.16, 1.17, 1.18, 1.19, 1.2, 1.21, 1.22, 1.23; 606/108, 191, 194, 195, 198

(56) References Cited

U.S. PATENT DOCUMENTS

| | | | |
|---|---|---|---|
| D359,802 S | 6/1995 | Fontaine | D24/155 |
| 5,591,197 A | 1/1997 | Orth et al. | 606/198 |
| D380,831 S | 7/1997 | Kavteladze et al. | D24/155 |
| 5,669,932 A | 9/1997 | Fischell et al. | |
| 5,695,516 A | * 12/1997 | Fischell et al. | 606/194 |
| 5,697,971 A | 12/1997 | Fischell et al. | 623/1 |
| D390,957 S | 2/1998 | Fontaine | D24/155 |
| 5,718,713 A | 2/1998 | Frantzen | 606/198 |
| 5,759,192 A | * 6/1998 | Saunders | 606/194 |
| 5,843,120 A | 12/1998 | Israel et al. | 606/198 |
| 5,895,406 A | 4/1999 | Gray et al. | 606/198 |
| 5,925,061 A | * 7/1999 | Ogi et al. | 606/198 |

FOREIGN PATENT DOCUMENTS

| | | |
|---|---|---|
| DE | 297 08 689 U1 | 8/1997 |
| EP | 0 758 541 A1 | 2/1997 |
| EP | 0 875 215 A1 | 11/1998 |
| JP | 10-165513 | 6/1998 |
| WO | 96/03092 | 2/1996 |
| WO | WO 97/25937 | 7/1997 |
| WO | WO 97/26840 | 7/1997 |
| WO | WO 97/32543 | 9/1997 |
| WO | WO 97/32544 | 9/1997 |
| WO | WO 97/40780 | 11/1997 |
| WO | WO 97/40781 | 11/1997 |
| WO | WO 97/40782 | 11/1997 |
| WO | WO 97/40783 | 11/1997 |
| WO | WO 97/40784 | 11/1997 |
| WO | WO 98/18405 | 5/1998 |
| WO | WO 98/18406 | 5/1998 |
| WO | 98/48734 | 11/1998 |
| WO | 99/02105 | 1/1999 |
| WO | 99/11197 | 3/1999 |

* cited by examiner

Primary Examiner—Henry J. Recla
Assistant Examiner—Vy Q. Bui
(74) Attorney, Agent, or Firm—Vidas, Arrett & Steinkraus

(57) ABSTRACT

A generally cylindrical, radially expandable stent may be composed of a plurality of interconnected multibonate cell structures. The cells have three or more enlarged end portions radiating from a common center within the cell. The cells may be of tribonate or higher order multibonate configuration. Stents composed up of a series of generally multibonate cell elements are also disclosed.

34 Claims, 27 Drawing Sheets

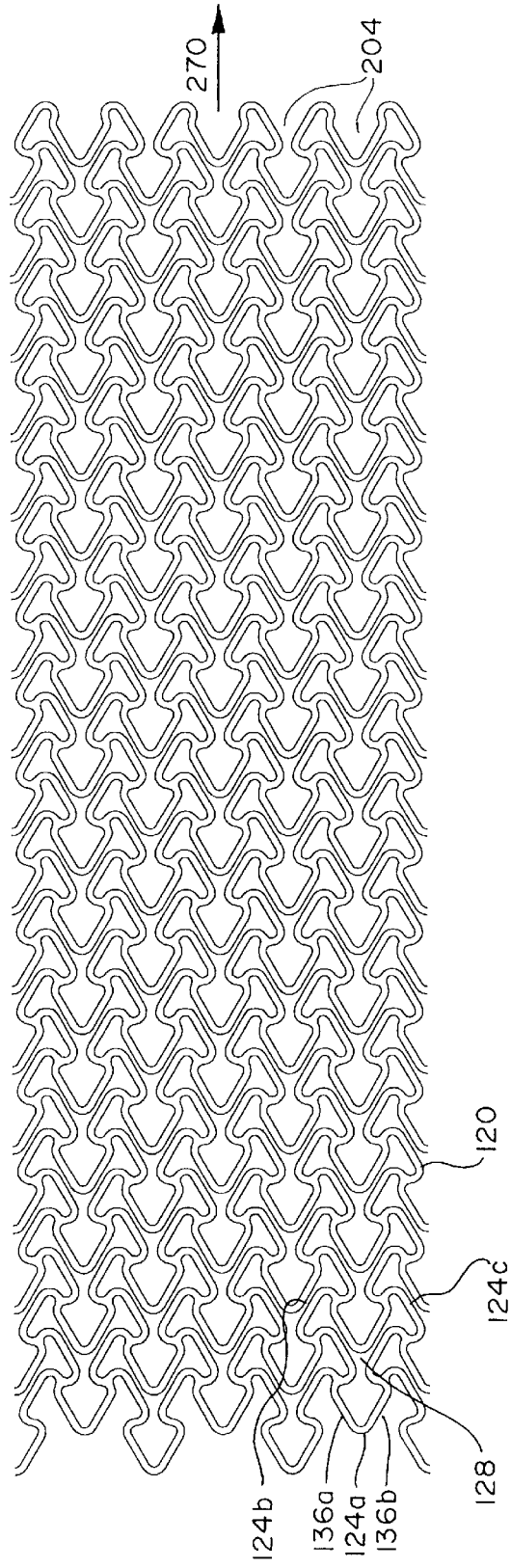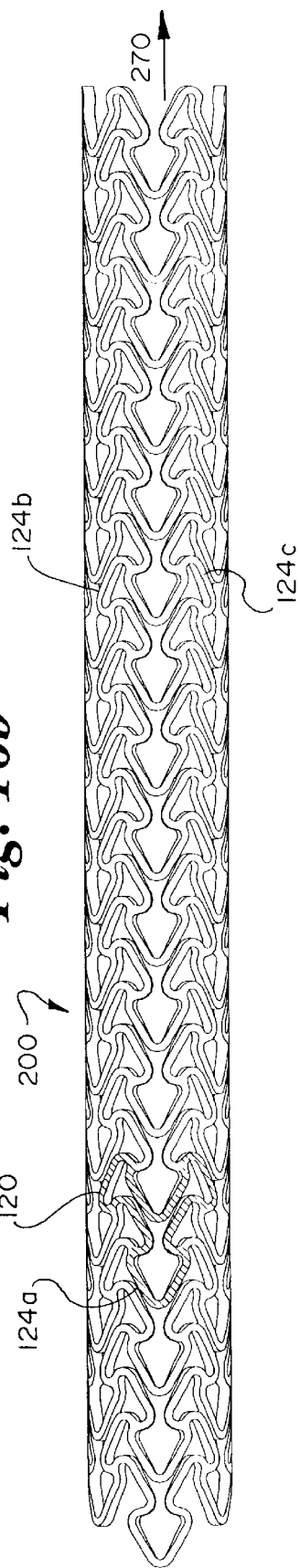

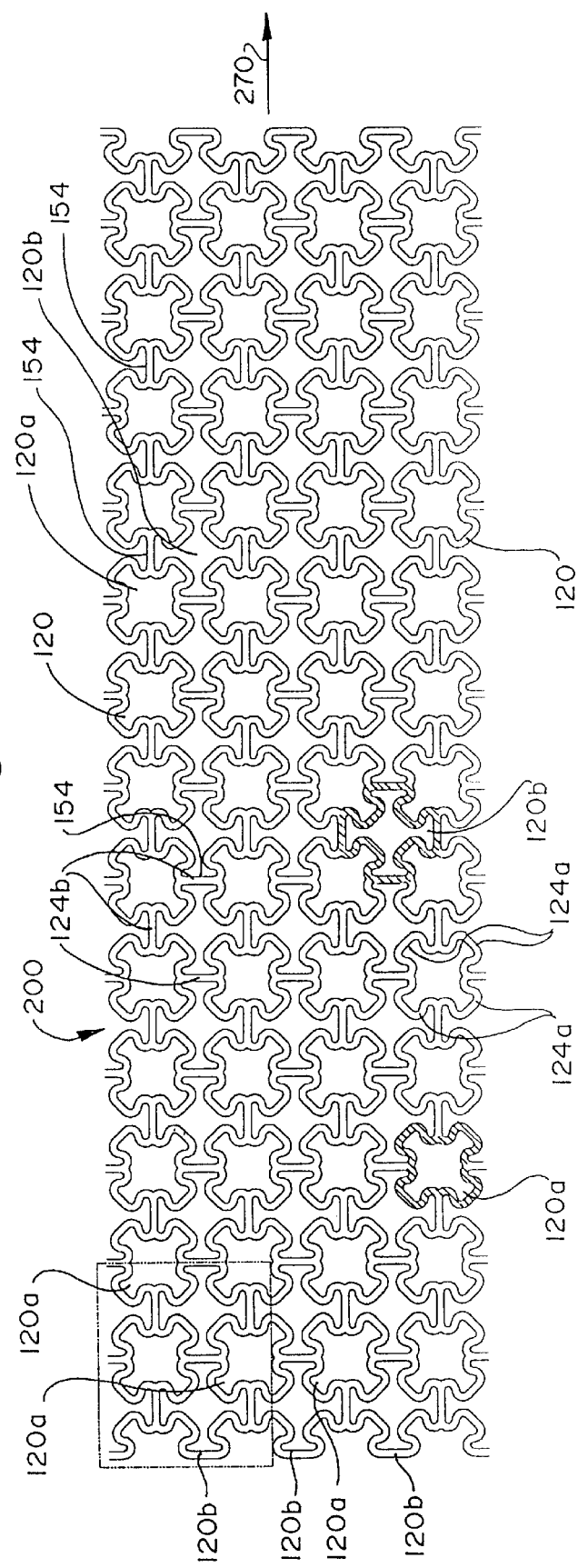

STENT CELL CONFIGURATIONS

This application is a continuation-in-part of U.S. application Ser. No. 09/036,665 filed Mar. 4, 1998 now abandoned, the contents of which is incorporated herein in its entirety by reference.

BACKGROUND OF THE INVENTION

1. Field of the Invention

This invention relates to stents of improved cell configuration.

2. Brief Description of the Prior Art

Stents are radially expandable endoprostheses which are typically intravascular implants capable of being implanted transluminally and enlarged radially after being introduced percutaneously. They have also been implanted in urinary tracts and bile ducts. They are used to reinforce body vessels and to prevent restenosis following angioplasty in the vascular system. They may be self-expanding or expanded by an internal radial force, such as when mounted on a balloon.

In the past, stents have been generally tubular but have been composed of many cell configurations and have been made of many materials, including metals and plastic. Ordinary metals such as stainless steel have been used as have shape memory metals such as Nitinol and the like. Stents have also been made of biodegradable plastic materials. Such stents have been formed from wire, tube stock, and the like.

SUMMARY OF THE INVENTION

This invention provides new configurations of the cells making up stents which may be adapted to all of the various types of prior art stents described above and/or known previously in the art. In general, as will be seen from the embodiments described hereinafter, the improved cell configurations are generally trichotomous, i.e., divided into three parts. More particularly, the cells are of a triskelion-like or trifurcate configuration, i.e., composed of three parts with axes of each part radiating from a common center. There are numerous advantages to the new configurations. For example, the configurations of the invention limit recoil and add resistance to compression for an expanded stent and provides increased side branch access, among other things. Also, the stents of this invention are longitudinally flexible.

The invention is also directed to a stent of generally cylindrical shape composed of at least one multibonate cell structure and desirably of a plurality of interconnected multibonate cell structures, as defined below. The multibonate structures may be interlocking and may be regularly arranged.

The invention contemplates stents having only one type of multibonate cell structure present as well as stents having a plurality of different multibonate cell structures present. Stents comprised of a plurality of multibonate cell structures of different order are also contemplated.

The invention is also directed to a stent comprised of a plurality of interlocking cell structures selected from the group consisting of bonate cell structures oriented at an oblique angle relative to the longitudinal axis of the stent, multibonate cell structures and combinations thereof.

BRIEF DESCRIPTION OF THE FIGURES

FIG. 14b is a flat plan view showing the rotational axis of symmetry of the multibonate cells of FIG. 14a;

FIG. 14c is a flat plan view showing the planes of reflectional symmetry of the multibonate cells of FIG. 14a;

FIG. 15b is a flat plan view showing the plane of reflectional symmetry of the multibonate cells of FIG. 15a;

FIG. 16a is a flat plan view showing yet another tribonate embodiment of the invention;

FIG. 16b is a side elevational view of the stent of FIG. 16a;

FIG. 16c is a three dimensional isometric view of the stent of FIG. 16a;

FIG. 19 is a flat plan view showing a quadribonate embodiment of the invention;

FIG. 22b is an enlarged portion of FIG. 22a; and

DETAILED DESCRIPTION

Figure 1:
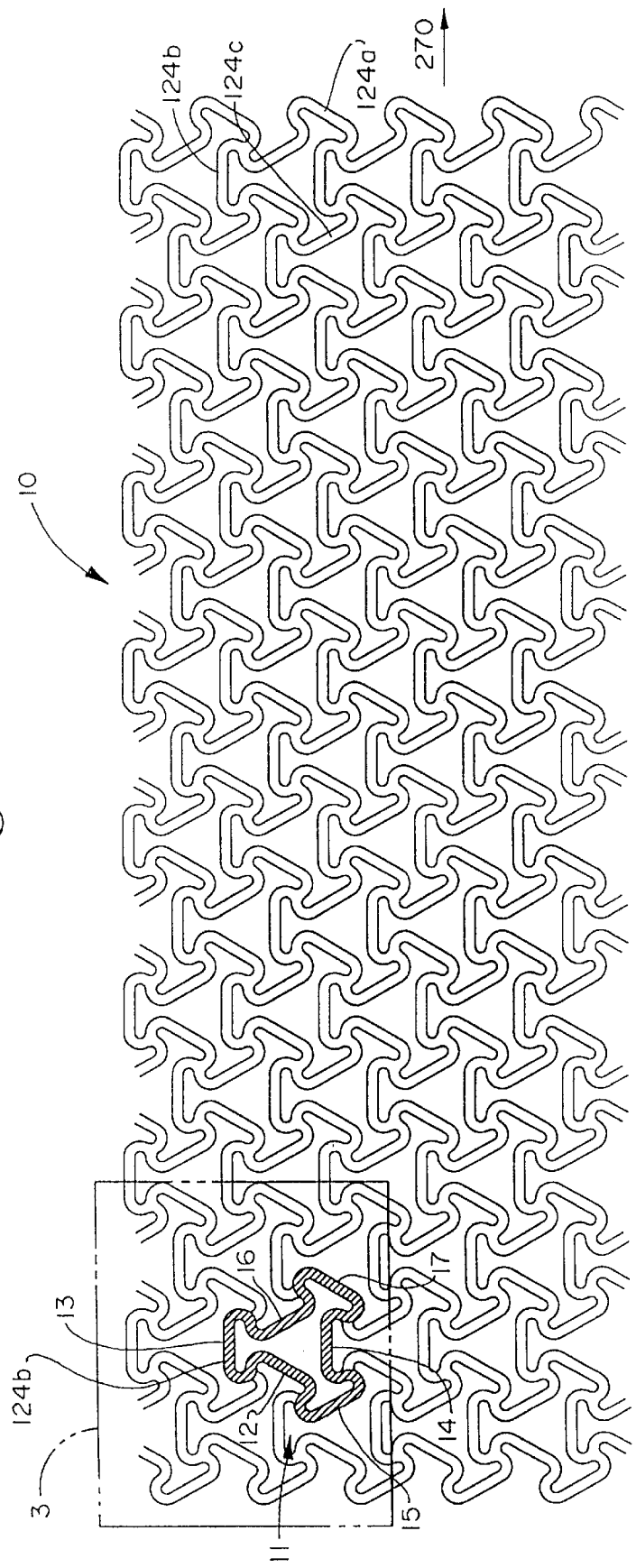
FIG. 1 is a flat plan view of an embodiment of a stent configuration of the invention in the unexpanded condition in which the cells share common elements.
Figure 2:
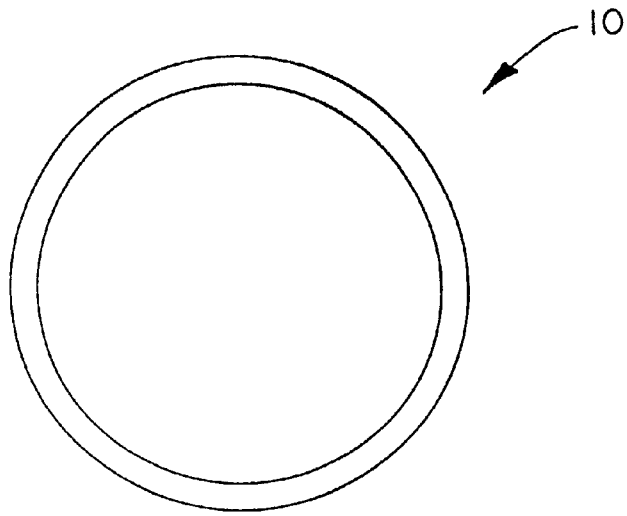
FIG. 2 is an end view of a tubular stent of FIG. 1 according to the invention in its normal unexpanded condition.
Figure 3:
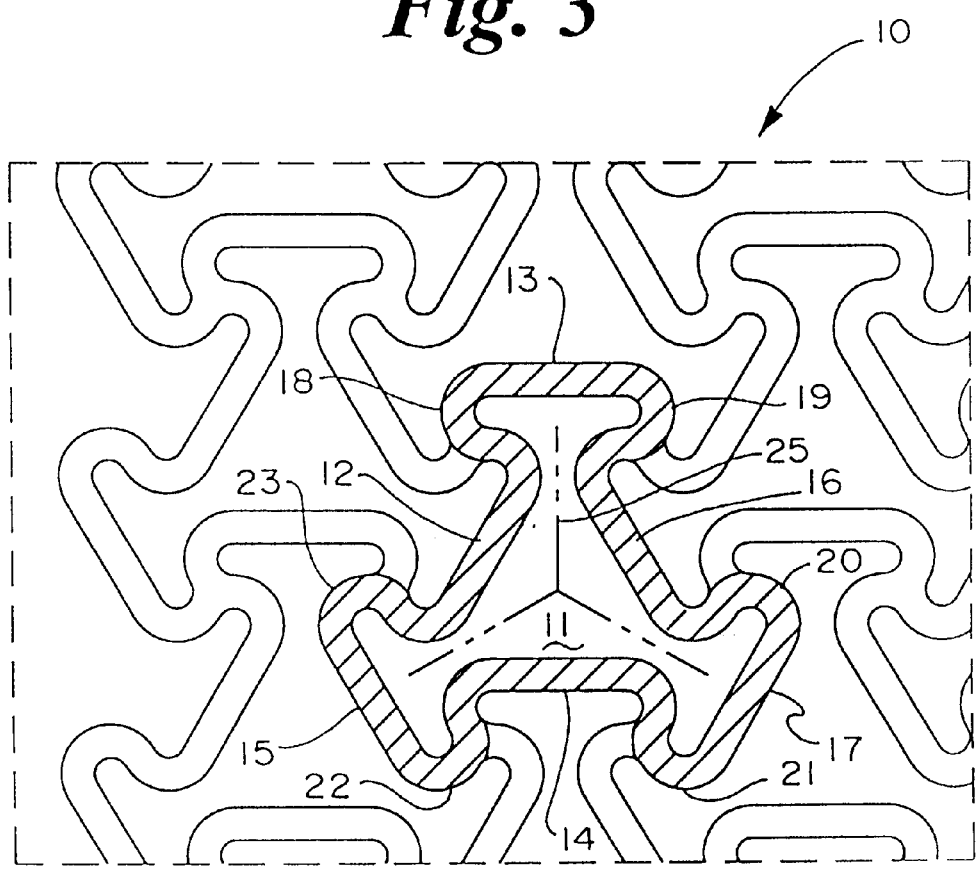
FIG. 3 is a detail view of a portion of FIG. 1, as indicated.

An embodiment of a generally cylindrical stent 10 according to the invention is illustrated in FIGS. 1–4. It comprises a metal tube as shown in the FIG. 2 end view, such as Nitinol, or stainless steel preferably, which has been etched or more preferably laser cut to the configuration shown in the flat plan view of FIG. 1. The configuration may be formed in flat sheet, rolled into a cylinder and welded or the like, or the configuration may be formed directly from a small tube such as a hypotube. An enlarged detail of FIG. 1 is shown in FIG. 3. This configuration is made up of a series of generally triangular-like expansion cell elements generally indicated at 11 (see darkened cell in the Figures for clarity) having relatively straight segments 13, 15 and 17, relatively straight segments 12, 14 and 16 and curvilinear segments 18–23. Segments 12, 14 and 16 comprise a first set of three segments arranged relative to each other in triangular spaced positions as shown in FIG. 3. Segments 13, 15 and 17 are placed in triangular spaced positions also but are outwardly positioned with respect to inwardly positioned segments 12, 14 and 16 and are placed opposite paired ends of 12/16, 16/14 and 12/14 as shown. In this embodiment these segments 12–17 are all straight. Curvilinear segments 18, 19, 20, 21, 22 and 23 interconnect segments 12/13, 13/16, 16/17, 14/17, 14/15 and 12/15 as shown. Preferably the segments are curvilinear, more preferably they are S-shaped as shown, although they can be made up of one or more straight sections. The resultant cell exhibits the triskelion configuration, having the three part axis 25 radiating from a common center. Cells 11 in this embodiment are arranged in an internested arrangement or network as shown in the Figures with adjacent cells sharing common sides or segments.

Finally, the longitudinal axis of the stent is indicated by reference numeral 270 in the above figures and in all of the remaining figures of the application.

Figure 4:
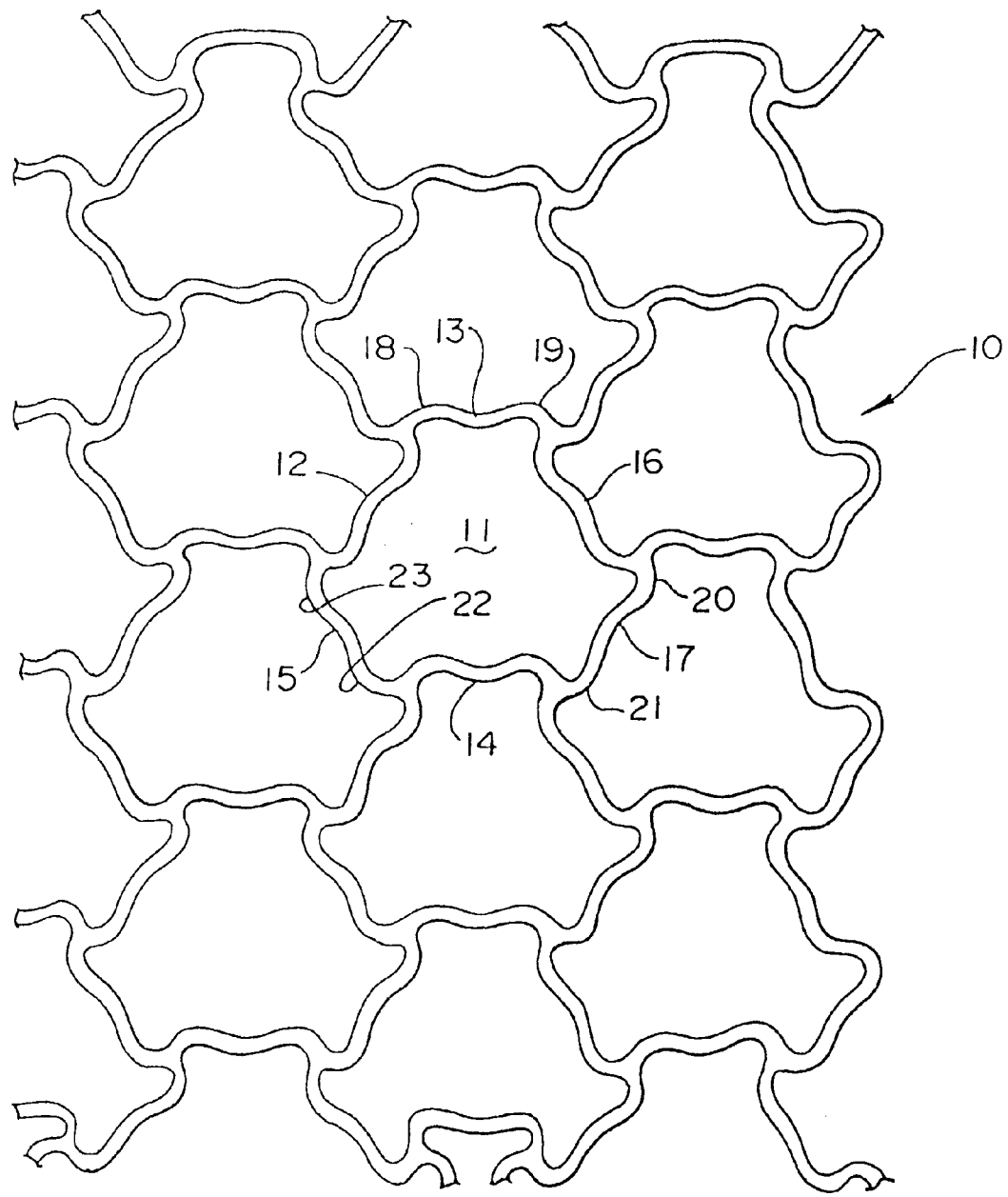
FIG. 4 is a view of the stent of FIGS. 1 and 2 showing the expanded condition.

When the stent of FIGS. 1 and 2 is expanded, as shown in FIG. 4, on a balloon for example (not shown), the cells 11 take on a new configuration as shown, the segments making up the stent being indicated by the same numbers as used in FIGS. 1 and 3.

Figure 5:
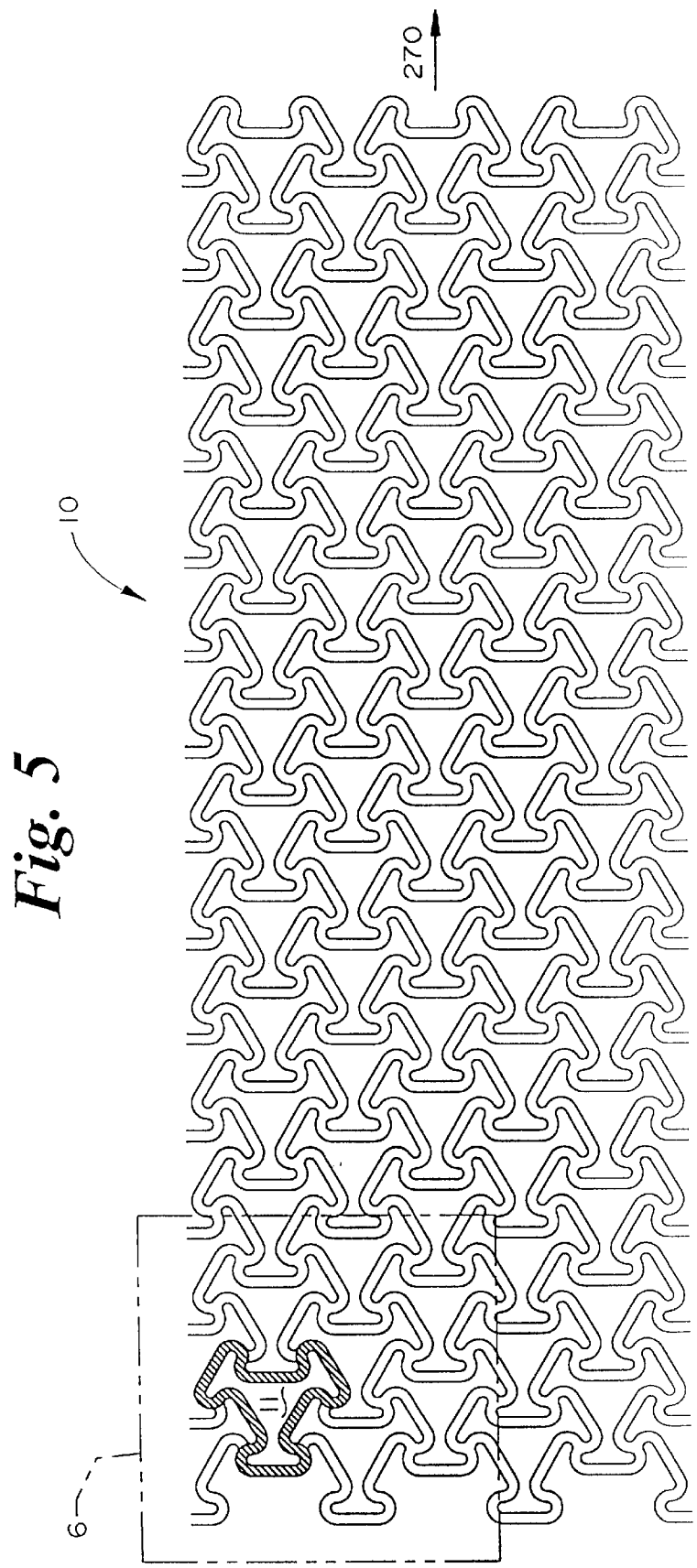
FIG. 5 is another embodiment of the invention, similar in view to that of FIG. 1, showing the flat plan of the stent in the unexpanded condition.
Figure 6:
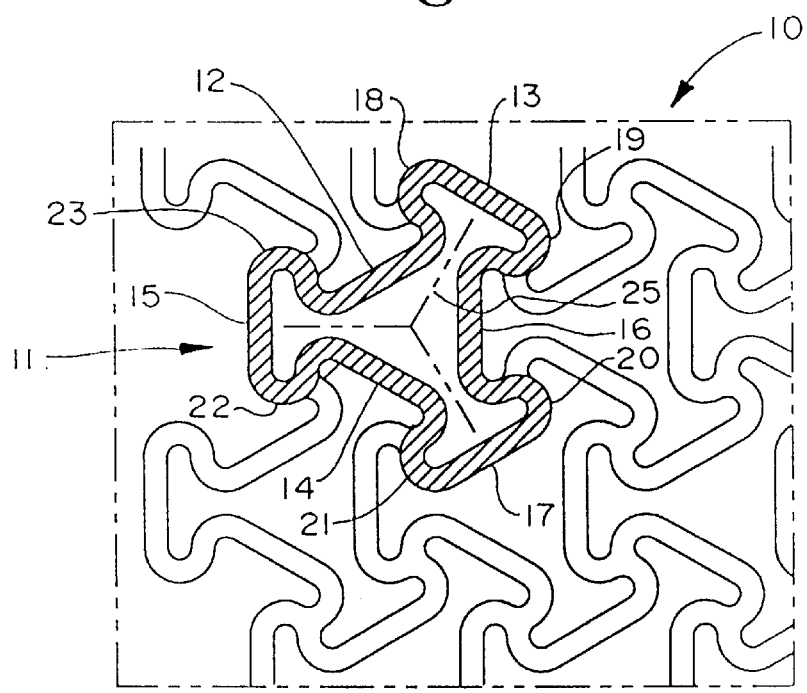
FIG. 6 is a detail view of a portion of FIG. 5, as indicated.

Referring now to FIGS. 5–6, another internested stent embodiment is shown. In this embodiment, as seen in FIGS. 5 and 6, expansion cells 11, best seen in the detail of FIG. 6 (again a cell is indicated by darkening) are shaped the same as cells 11 in FIGS. 1–3. However, they are skewed with respect to the longitudinal axis 270 of the stent rather than being arranged in parallel longitudinal lines in which the cells are positioned perpendicular to the longitudinal axis of the stent as in FIGS. 1–4.

Figure 7:
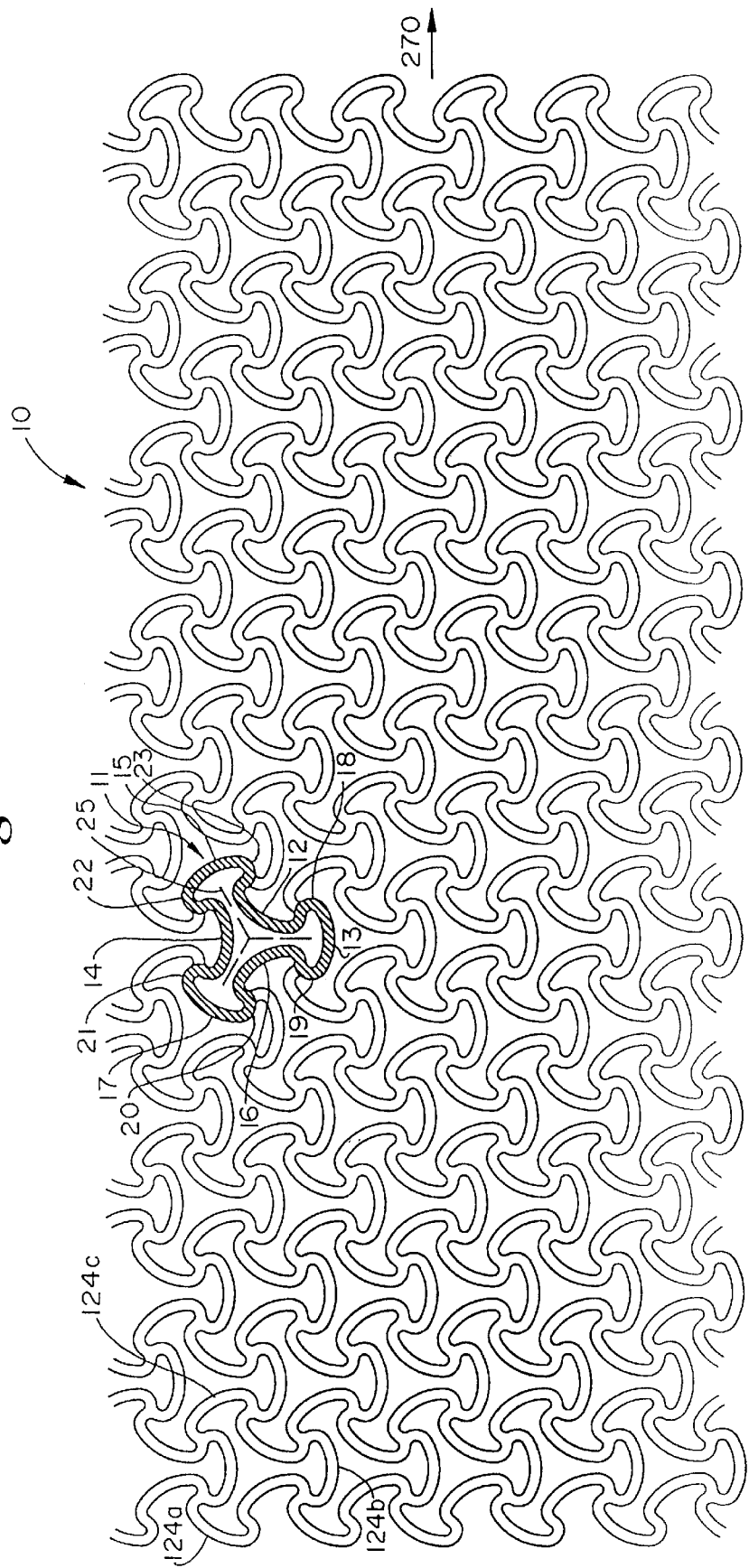
FIG. 7 is a flat plan view of another cell configuration according to the invention.

Referring now to FIG. 7, another cell configuration is shown to demonstrate that elements or segments 12, 14 and 16 need not be straight but may be arcuate as shown, either inwardly as shown in the Figure or outwardly.

Figure 8:
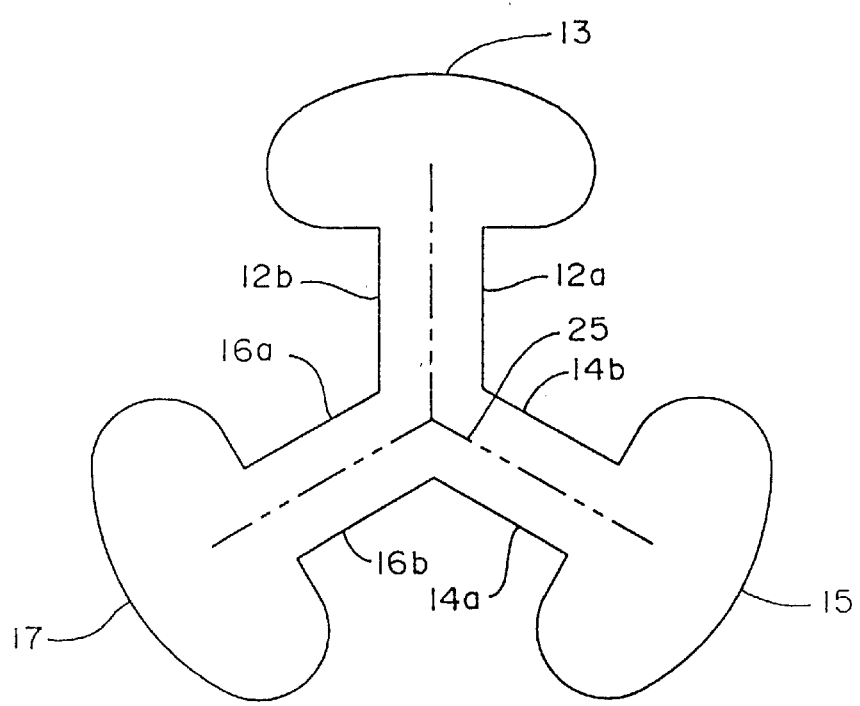
FIG. 8 is a schematic showing of yet another cell configuration.
Figure 9:
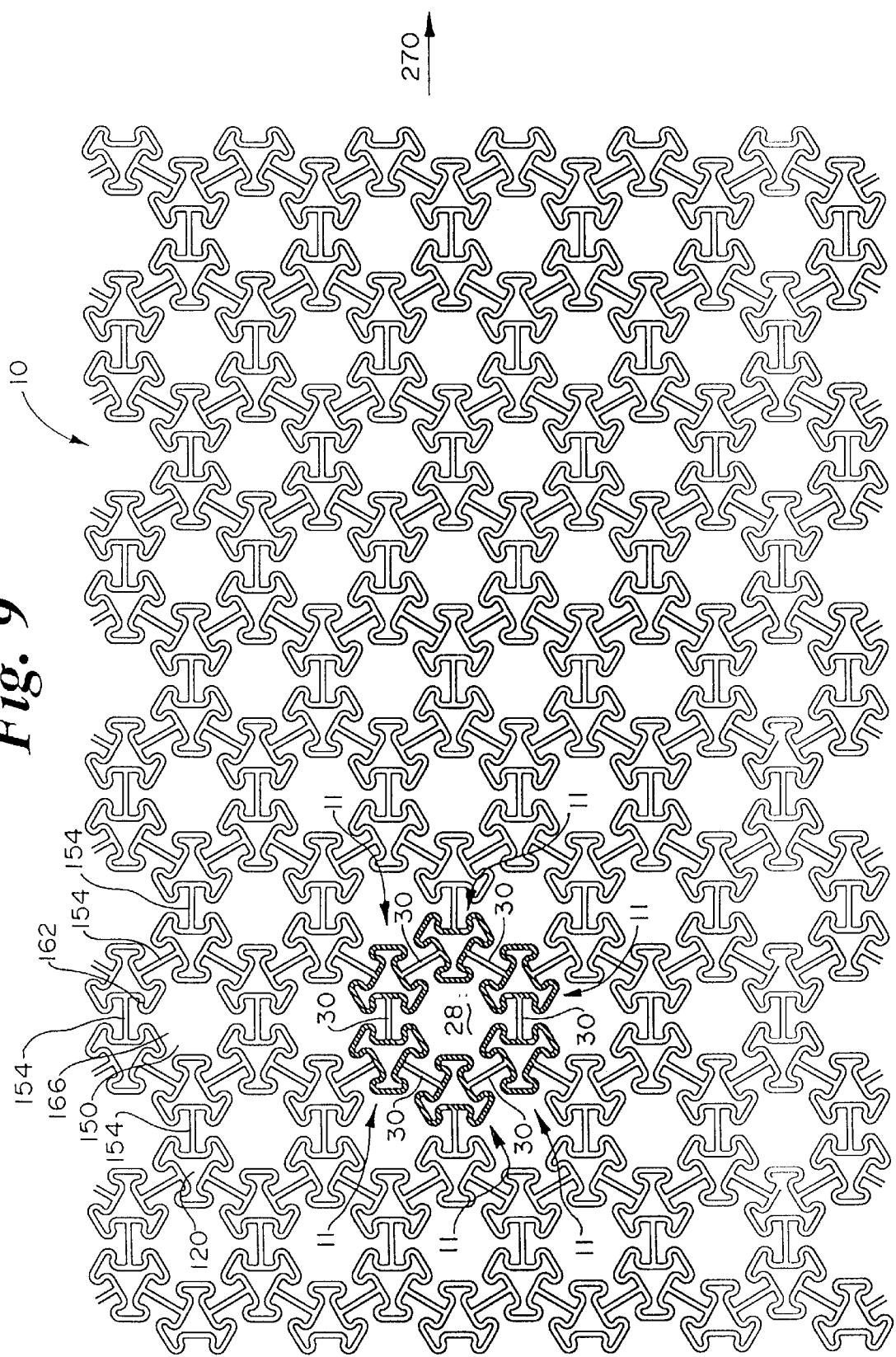
FIG. 9 is a flat plan view showing a form of interconnection between cells.
Figure 10:
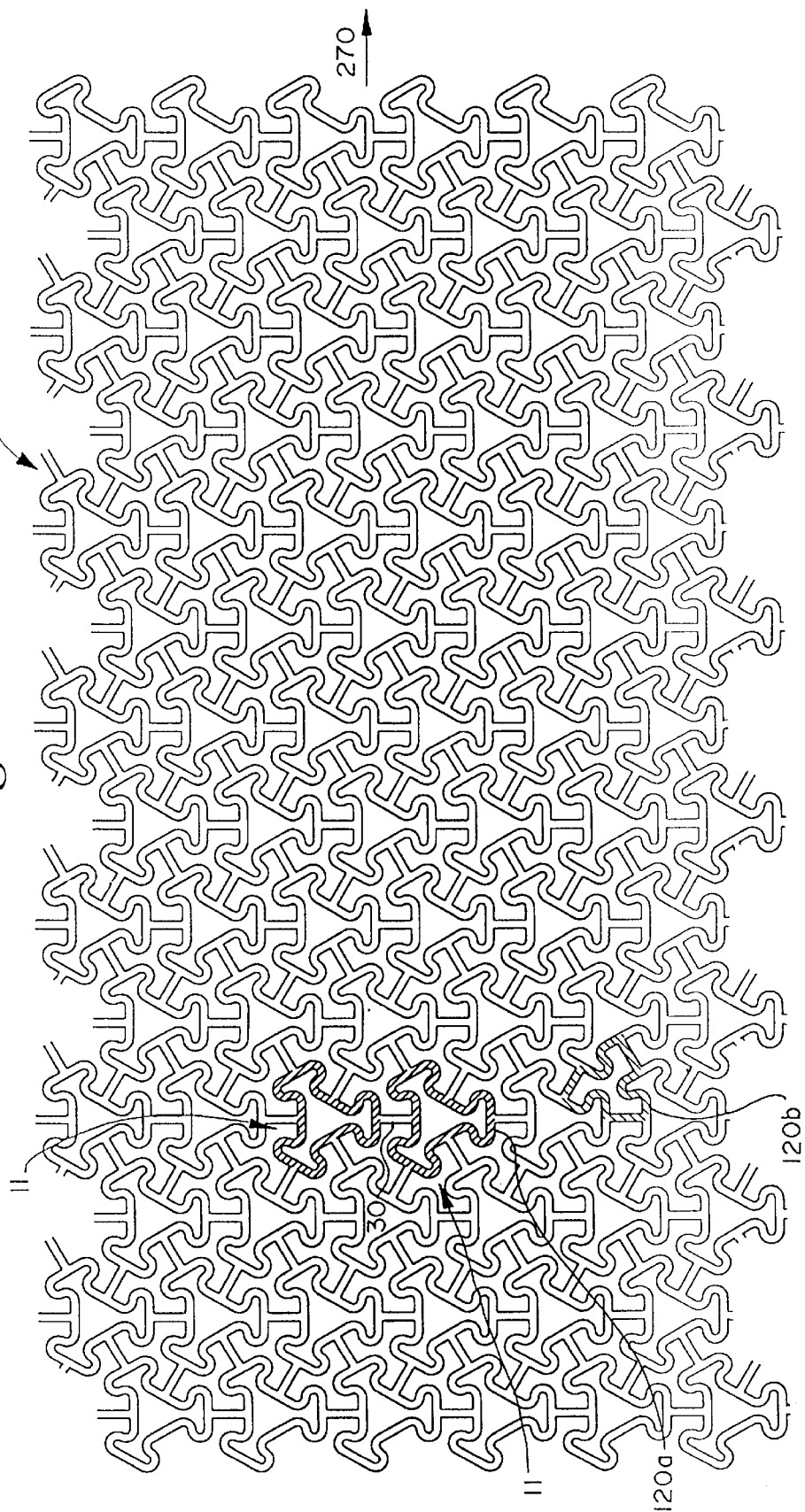
FIG. 10 is a flat plan view showing another form of interconnection between cells.

The cell configuration shown in FIG. 8 is a three-lobed configuration preferably used in an interconnected cellular arrangement with individual connecting members as discussed in FIGS. 9 and 10. In this embodiment three sections, 12a/12bm 14a/14bm and 16a/16b, radiate from a common center to terminate in enlarged end portions 13, 15 and 17, respectively. However, FIGS. 9 and 10 make use of cell configurations similar to those shown in FIGS. 1–6.

In FIG. 9, a series of sets of cells, each set consisting of six cells 11 arranged in a circular pattern 28, repeated throughout the stent body. Each cell 11 is connected to three adjacent cells 11 by three connector segments 30 in a repeating pattern through the stent body. In this particular arrangement, the connector members 30 extend from an inner segment on one cell to an inner segment on an adjacent cell, as shown. The connector members may be straight or curved and may be in various shapes such as zig-zag or S-shaped, etc.

In FIG. 10 the connector members 30 extend from an inner segment on one cell to an outer segment on the adjacent cell as shown. Cells 11 are arranged in vertical rows in this embodiment but are staggered longitudinally as can be seen in the Figures.

Figure 11:
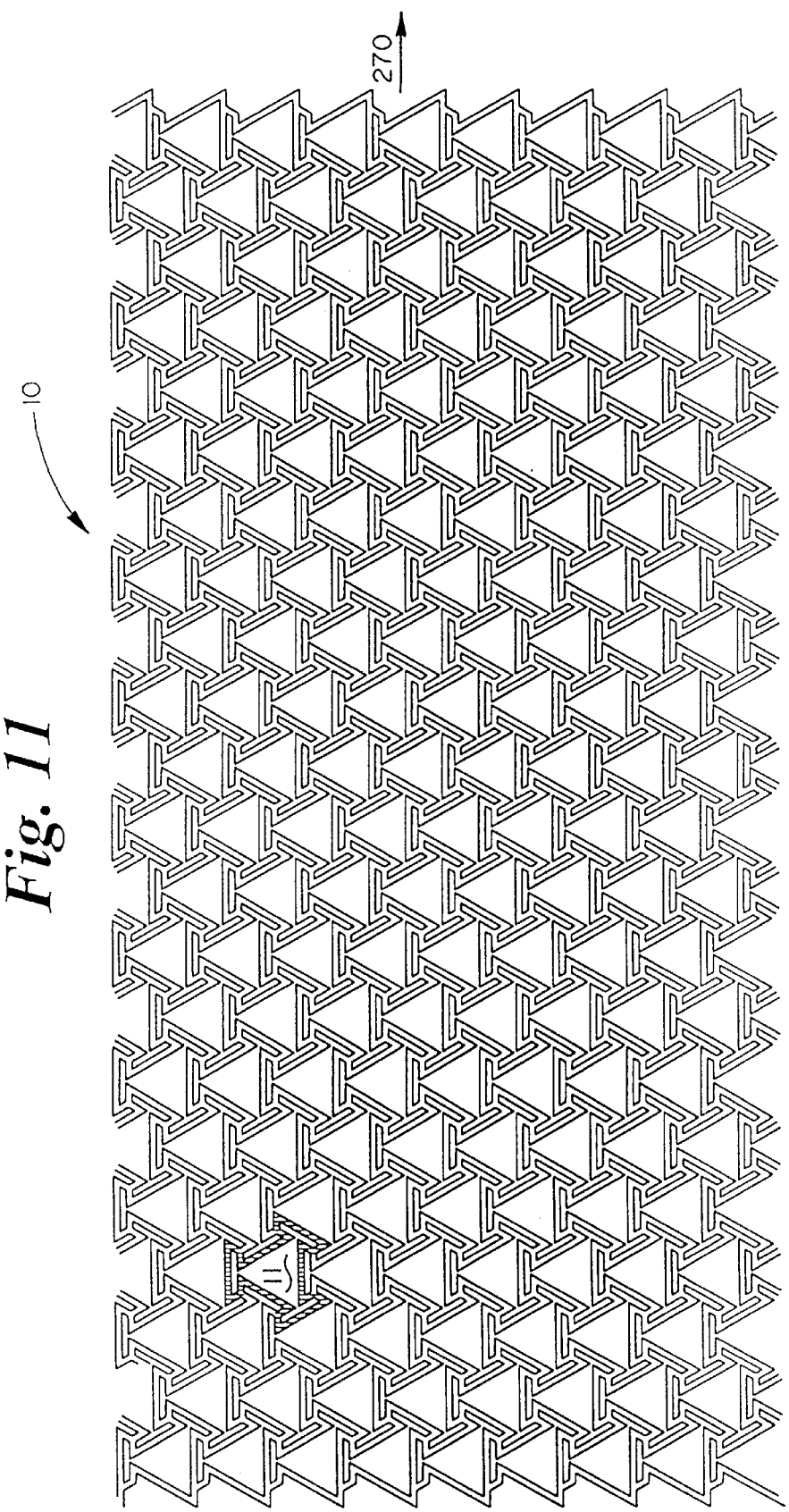
FIG. 11 is a flat plan view showing yet another embodiment of the invention.

FIG. 11 is illustrative of an internested stent configuration in which all segments of each cell are straight as opposed to curvilinear.

Figure 12:
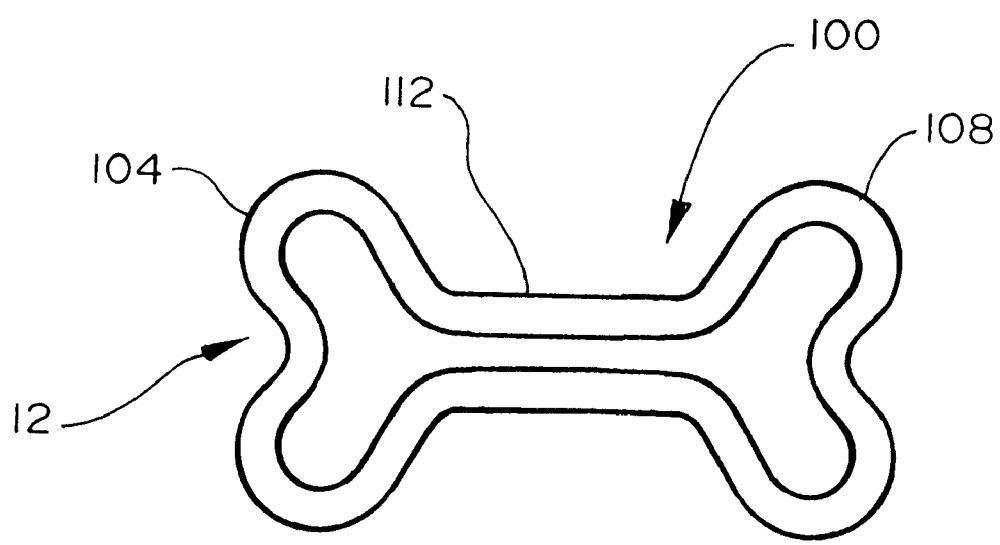
FIG. 12 is a flat plan view showing a bonate cell structure.

For the purposes of this disclosure, the term 'bonate' refers to a structure which has relatively wide end portions joined by a connecting portion which is, at least in part, relatively narrow. A bonate cell structure is illustrated generally at 100 in FIG. 12. Bonate cell structure 100 has a first relatively wide end portion 104 of the cell and a second relatively wide end portion 108 of the cell and a relatively narrow connecting portion 112 of the cell and resembles a dog bone. Connecting portion 112 may also be relatively narrow in only a portion thereof. Stents having bonate cell structures have been disclosed in commonly assigned U.S. application Ser. No. 08/947620 filed Oct. 9, 1997, the contents of which are incorporated herein in their entirety by reference.

Figure 13:
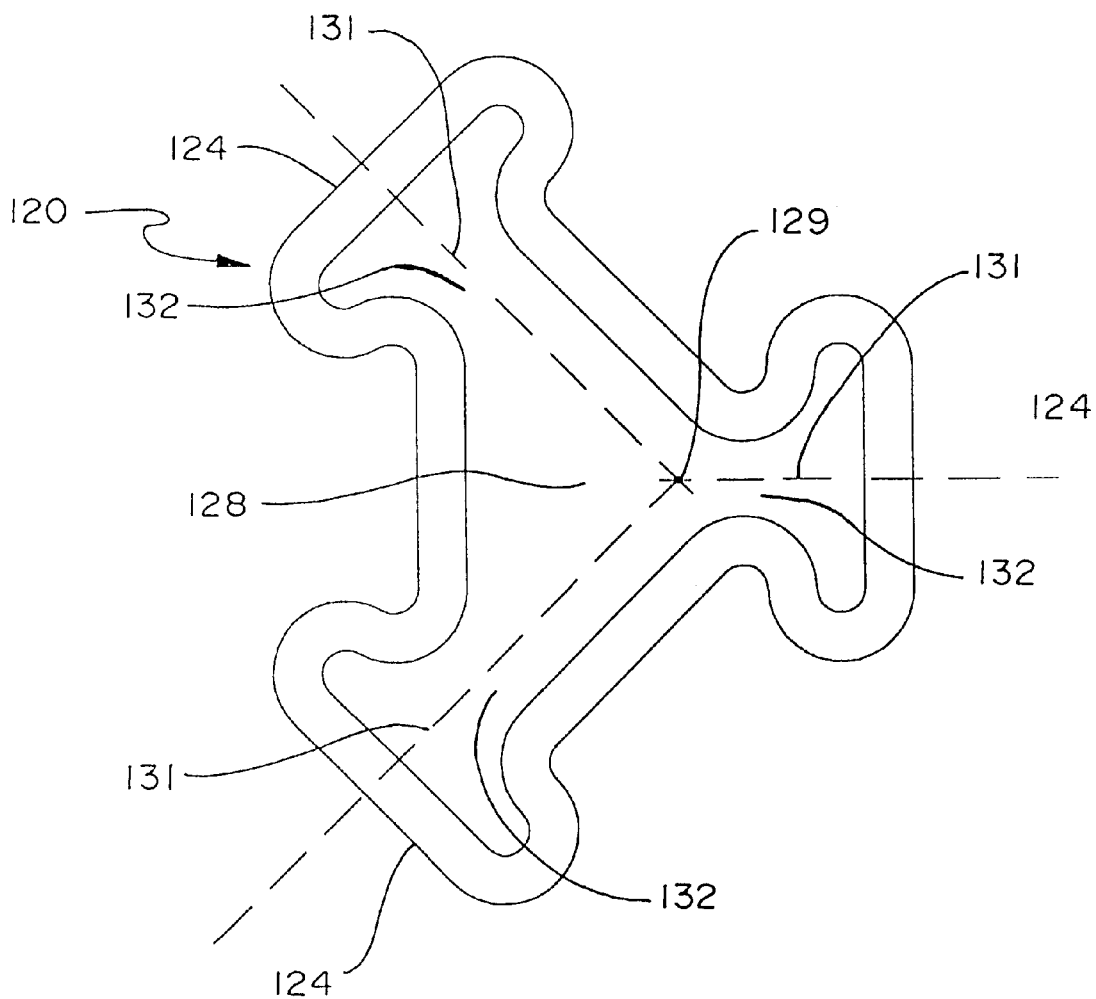
FIG. 13 is a flat plan view showing a multibonate (tribonate) cell structure.

The term 'multibonate', for the purposes of this disclosure, refers to a structure which has three or more relatively wide end portions each of which is joined to a common portion via a relatively narrow connecting portion. Further, each of the end portions radiates from at least one common point in the common portion, desirably in the center of the common portion. The relatively wide end portions of a multibonate structure may be lobe shaped. Also desirably, each of the end portions emanates from a vertex region of the common portion. One such multibonate cell structure is shown generally at 120 in FIG. 13. Multibonate structure 120 consists of three relatively wide end portions 124 of the cell each of which is joined to a common portion 128 of the cell via relatively narrow connecting portions 132 of the cell. It is noted that each of end portions 124 extends from a common point 129. It is also noted that each of end portions 124 extends from a vertex 131 of common portion 128. The multibonate structure of FIG. 13 is also termed a tribonate structure because of the presence of the three end portions. Multibonate structures with four relatively wide end portions would similarly be termed 'quadribonate' and multibonate structures with five, six, seven and eight relatively wide end portions would be termed 'pentibonate', 'hexibonate', 'heptabonate' and 'octabonate', respectively. A multibonate structure with 'n' end portions is referred to as an '$n^{th}$ order' multibonate structure.

The present invention is directed generally to stents formed of multibonate cell structures. In one embodiment, the invention is directed to a stent of generally cylindrical shape comprised of at least one multibonate cell structure and desirably of a plurality of interconnected multibonate cell structures. The multibonate cell structures may optionally be regularly arranged. One such stent is shown in the flat in FIG. 14a. Stent 200 consists of a plurality of interconnected tribonate cell structures 120. Tribonate cell structures are arranged in interconnected longitudinal rows 204. Tribonate cell structures within a row are seen to be tessellated or interlocking with adjacent cell structures having at least one member 124a in common. Member 124 simultaneously serves as an end portion of a cell structure and as a portion of the central portion of a cell structure. Tribonate cell structures 120 in adjacent rows 204 are also seen to share a member 124b in common. Member 124b, similarly, serves as an end portion in one cell structure and as a portion of the central portion of a cell in an adjacent row. All of the tribonate structures 120 in adjacent rows 204 of multibonate structures are identically oriented relative to the longitudinal axis of the stent.

Figure 14A:
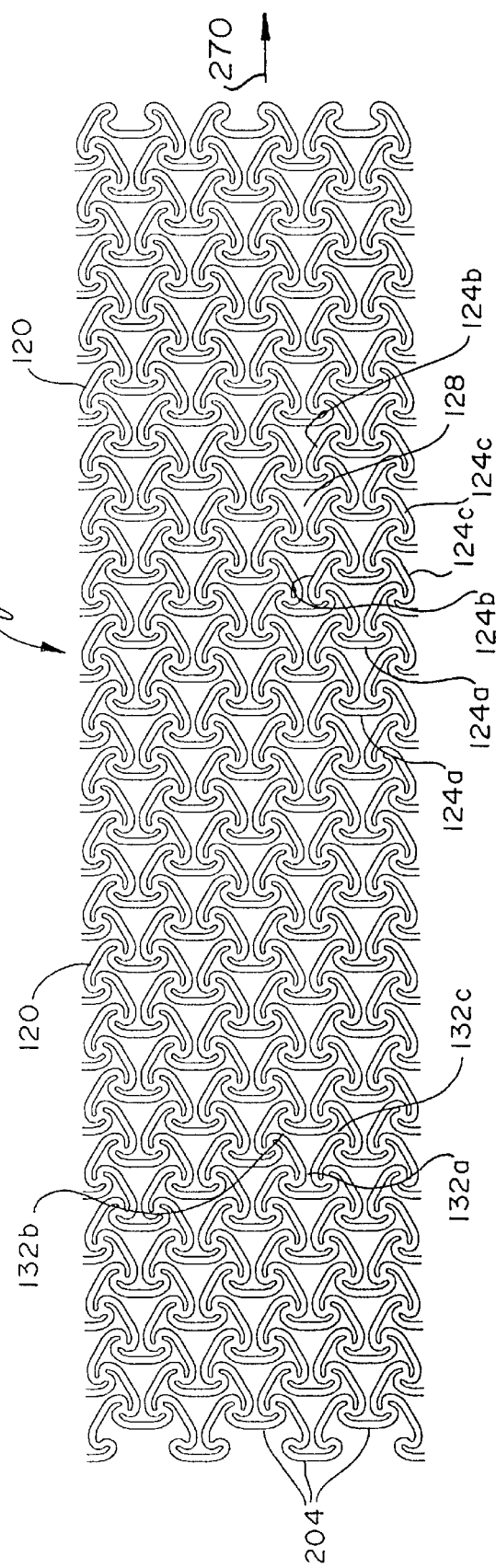
FIG. 14a is a flat plan view showing yet another tribonate embodiment of the invention.
Figure 14C:
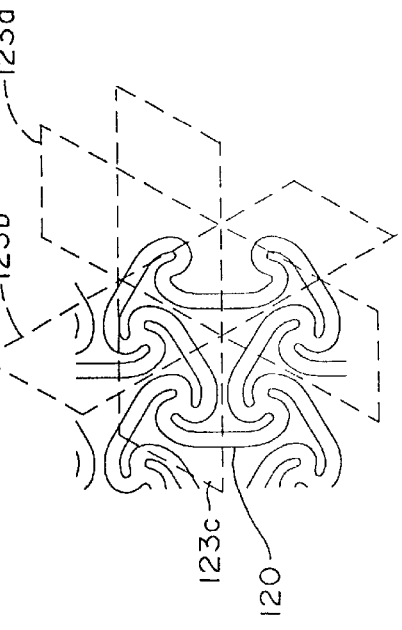
Figure 14B:
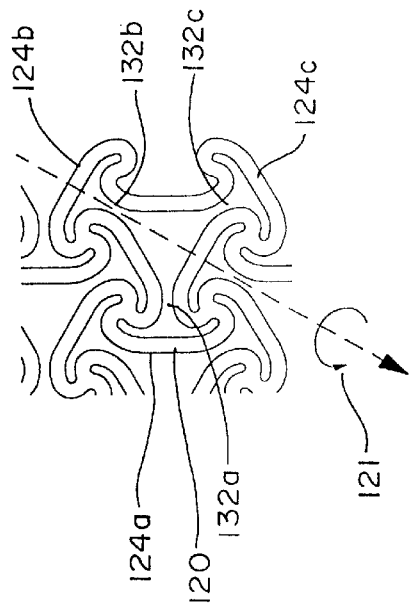

It is further noted that tribonate cells 120 of FIG. 14a have a common portion 128 which is substantially triangular and moreover formed substantially in an equilateral triangle. Each tribonate cell 120 has a threefold rotational axis of symmetry ($C_3$ axis of symmetry) 121 in the flat, through the center of the cell, as sown in FIG. 14b. Each tribonate structure further is characterized by three planes of reflectional symmetry ($\sigma_v$) 123a–c, as shown in FIG. 14c. To that end, first, second and third end portions 124a–c, respectively, are the same shape. Moreover, all three connecting portions 132a–c are substantially the same shape, width and length.

Figure 15A:
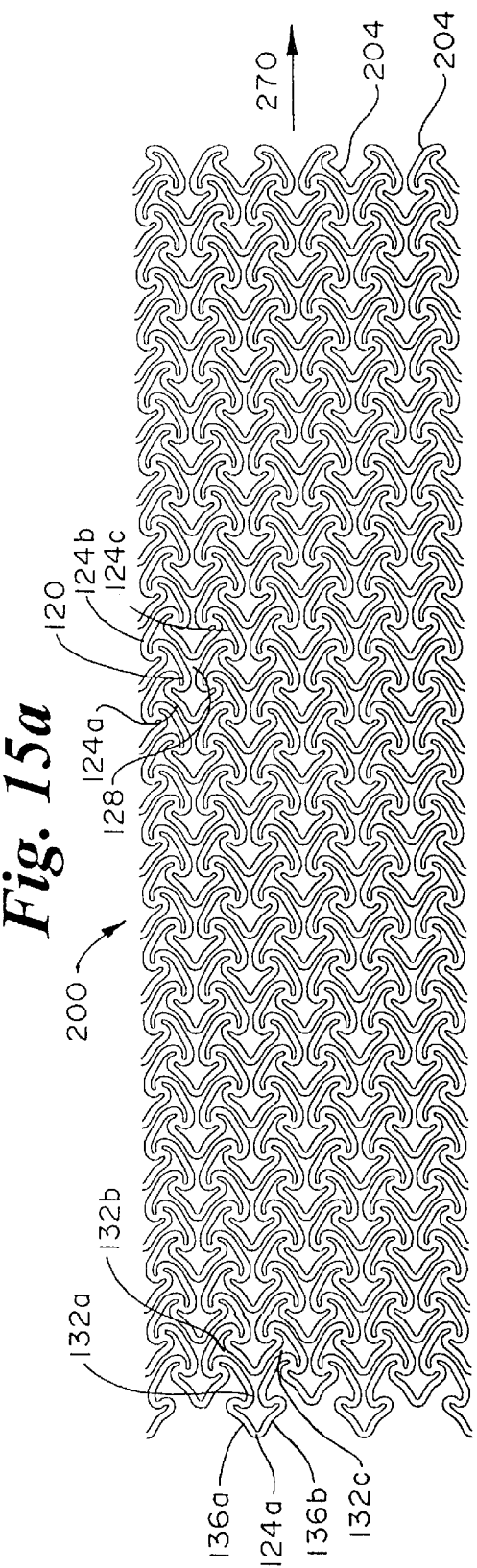
FIG. 15a is a flat plan view showing yet another tribonate embodiment of the invention.
Figure 15B:
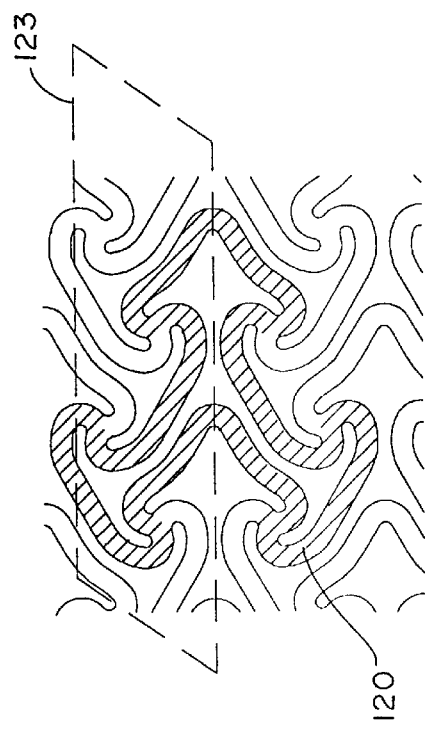
Figure 16C:
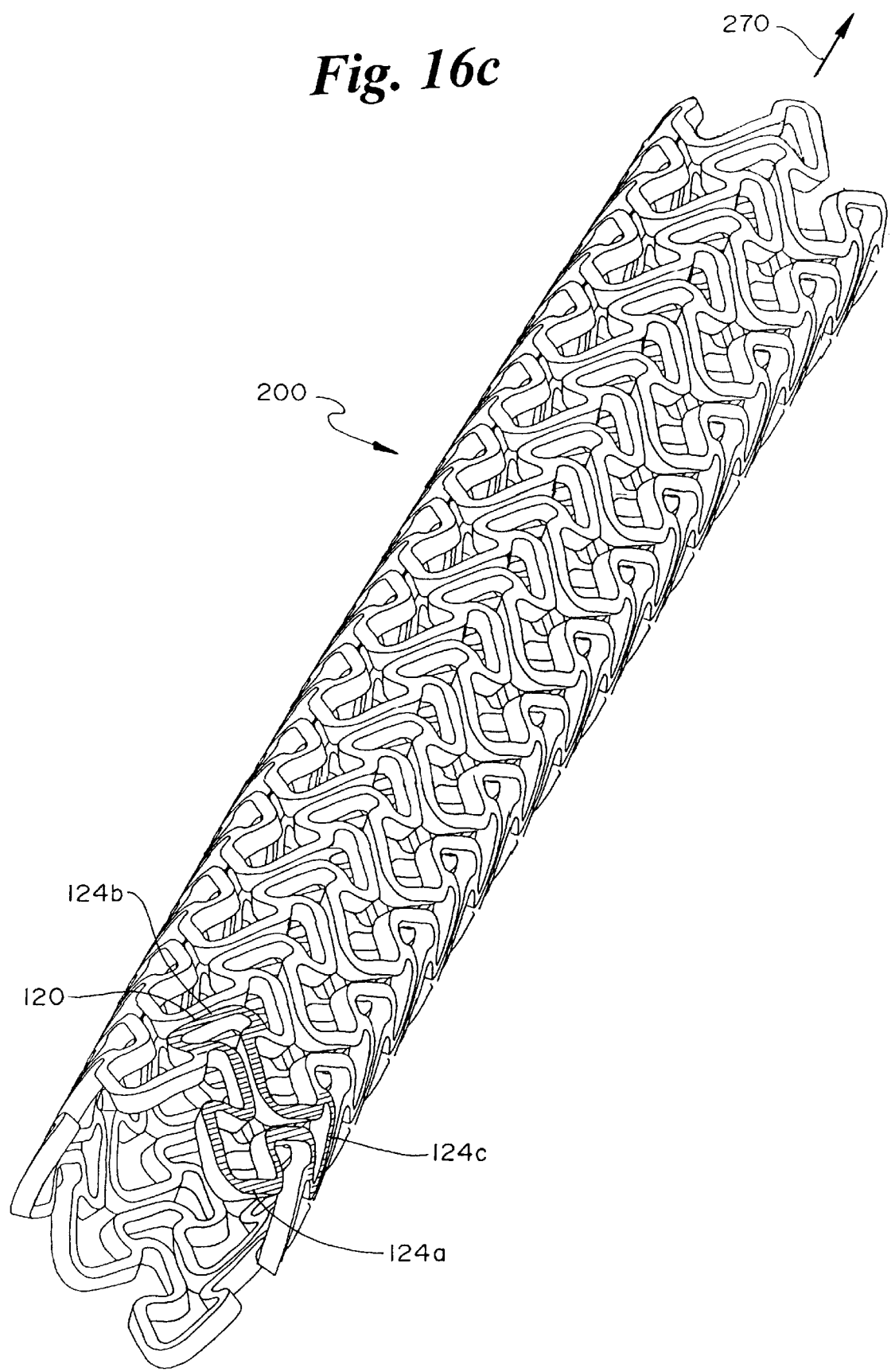
Figure 16D:
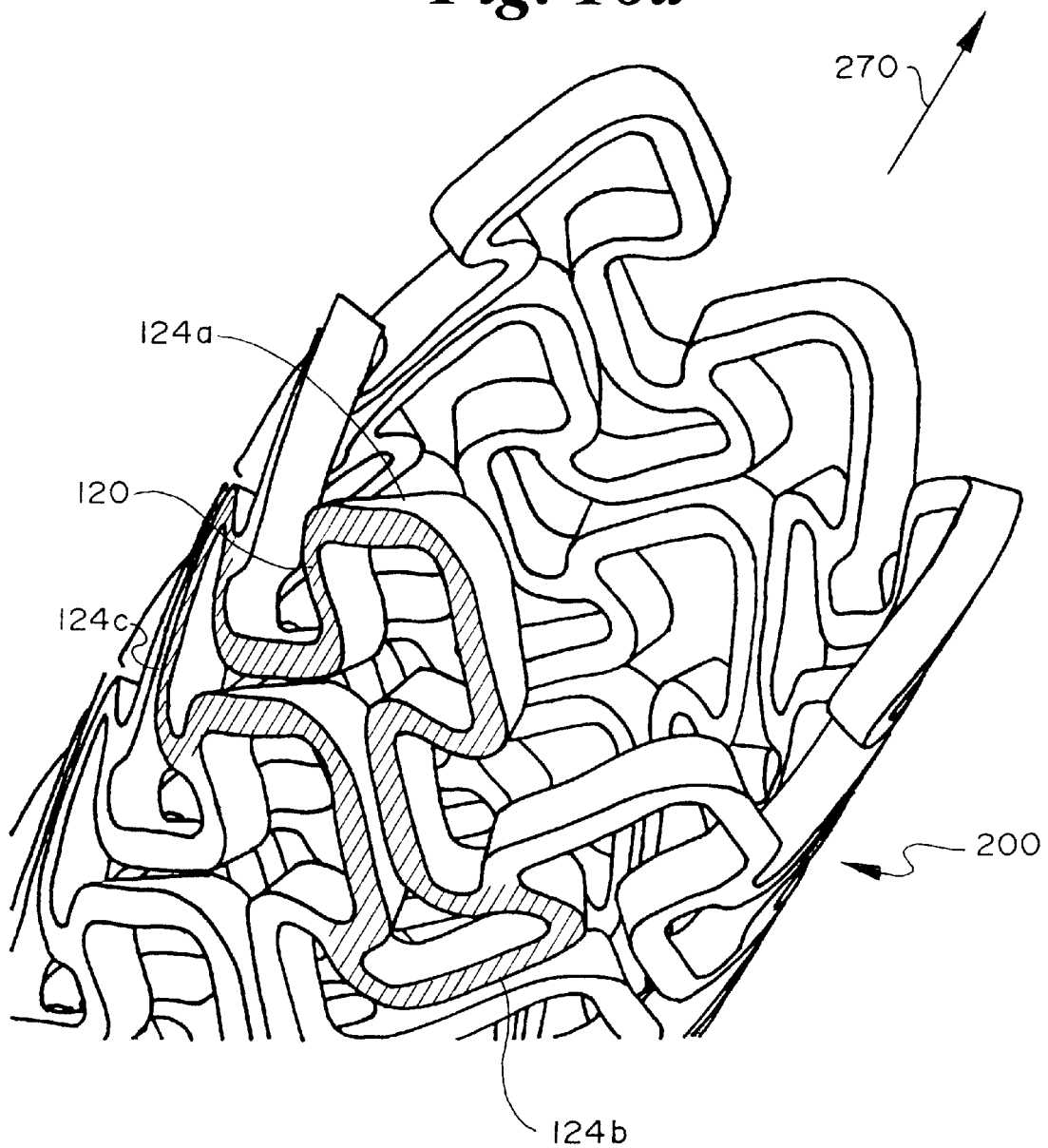
FIG. 16d is a magnified view of an end portion of the stent as shown in FIG. 16d.
Figure 16E:
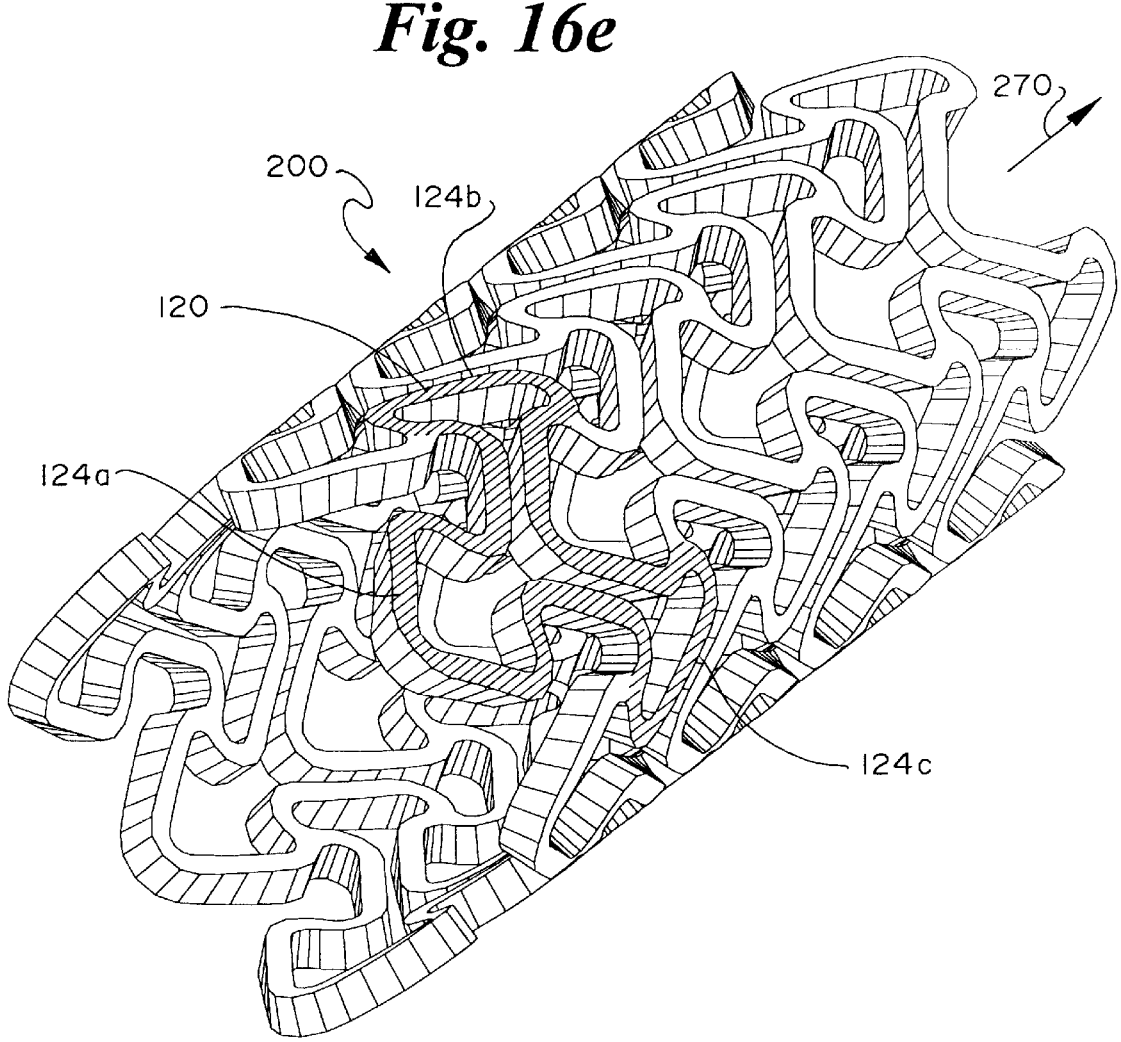
FIG. 16e is a three dimensional isometric view of a stent similar to that of FIG. 16c, but shorter.

The invention further contemplates variations on the multibonate structure in general and the tribonate structure in particular. One such variation is shown in stent 200 in FIG. 15a. Tribonate cell structure 120 is not seen to possess the threefold rotational symmetry of the tribonate cell structure of FIG. 14a. Moreover, cells 120 are seen to possess only a single plane of reflectional symmetry ($\sigma_v$) 123, as shown in FIG. 15b. The cell structure is also seen to vary in that second and third end portions 124b,c are a reflection of one another while end portion 124a differs in shape. End portion 124a is substantially triangular in shape. Its boundaries are defined by two convex side portions 136a,b. End portions 124b,c are each seen to be mushroom shaped. Each of end portions 124a–c extend from connecting portions 132a–c, respectively, which in turn, extend from common portion 128. End portions 124a–c are seen to be mushroom shaped.

Another embodiment of the invention is shown generally at 200 in FIGS. 16a–e. As in FIG. 15, tribonate cell structure 120 does not possess the threefold rotational symmetry of the tribonate cell structure of FIG. 13. Moreover, cells 120 are seen to possess only a single plane of reflectional symmetry ($\sigma_v$) The cell structure is also seen to vary in that second and third end portions 124b,c are a reflection of one another while end portion 124a differs in shape. End portion 124a is substantially triangular in shape. Its boundaries are defined by two substantially straight side portions 136a,b. End portions 124b,c are each slot shaped.

Figure 17:
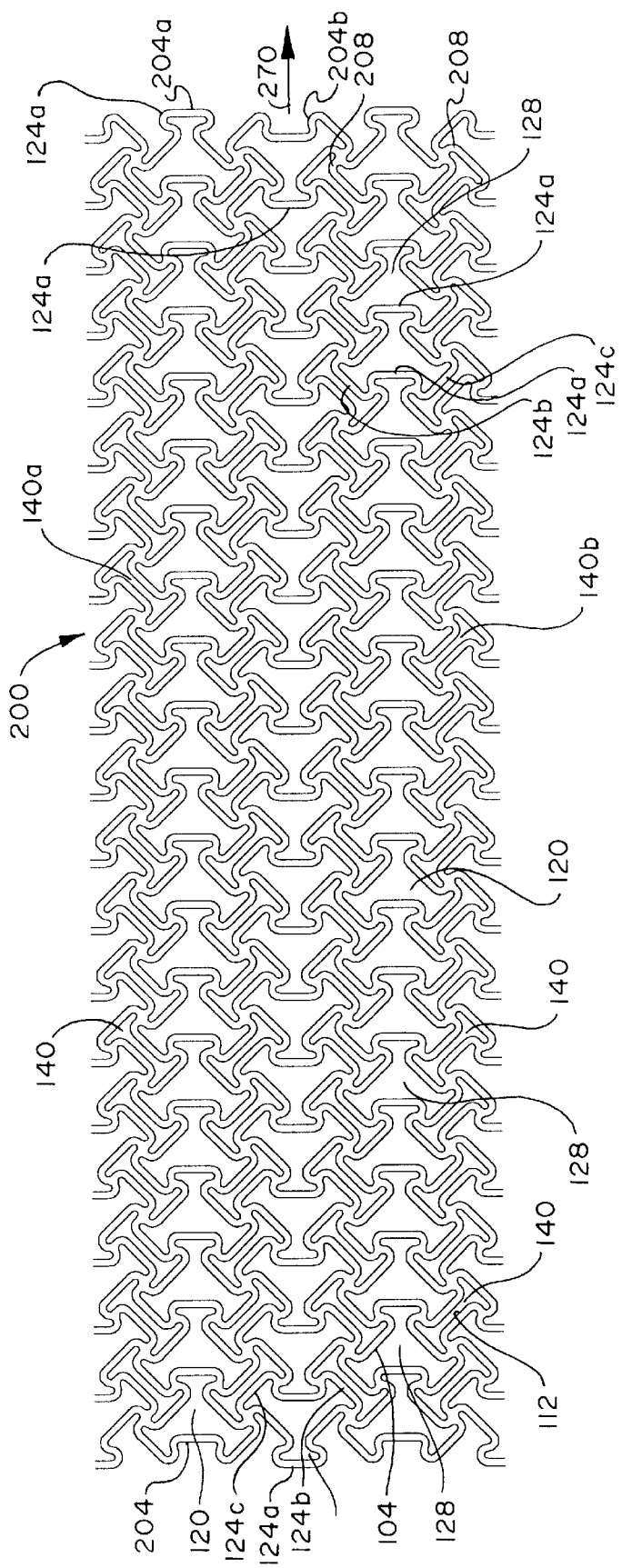
FIG. 17 is a flat plan view showing yet another embodiment of the invention which includes tribonate and bonate structures.

In another embodiment, the invention is directed to a stent, as shown generally at 200 in FIG. 17. Stent 200 is composed of a plurality of connected tribonate cell structures 120 arranged in longitudinal rows 204. The stent further comprises a plurality of bonate cell structures 140 arranged in longitudinal rows 208 and extending between adjacent rows 204 of tribonate cells 120. Bonate cell structures 140 serve as connectors between adjacent rows of multibonate cells. Bonate cell structures 140 are disposed at an oblique angle relative to the longitudinal axis of the stent. Adjacent rows of bonate cell structures 140 are disposed at equal but opposite angles relative to the longitudinal axis 270 of the stent 200. Bonate cell structures 140 and multibonate cell structures 120 are seen to interlock with one another. End portions 104 of bonate structures 140 form a portion of the side of common portion 128 of tribonate cell structures 120. Similarly, end portions 124b,c of tribonate cell structures 120 form a portion of narrow connecting portion 112 of bonate cell structures 140. Within a longitudinal row 204 of tribonate structures, adjacent tribonate cell structures interlock as well with end portion 124a of a cell forming a part of common portion 128 of an adjacent cell.

The stent of FIG. 17 also differs from the previously shown stents in that tribonate cell structures in adjacent row 204 of tribonate cell structures are oppositely oriented—the cell structures in adjacent rows are rotated by 180° relative to one another. For example, end portions 124a of cell structures in row 204a is directed in an opposite direction relative to end portions 124a of cell structures in row 204b.

Figure 18:
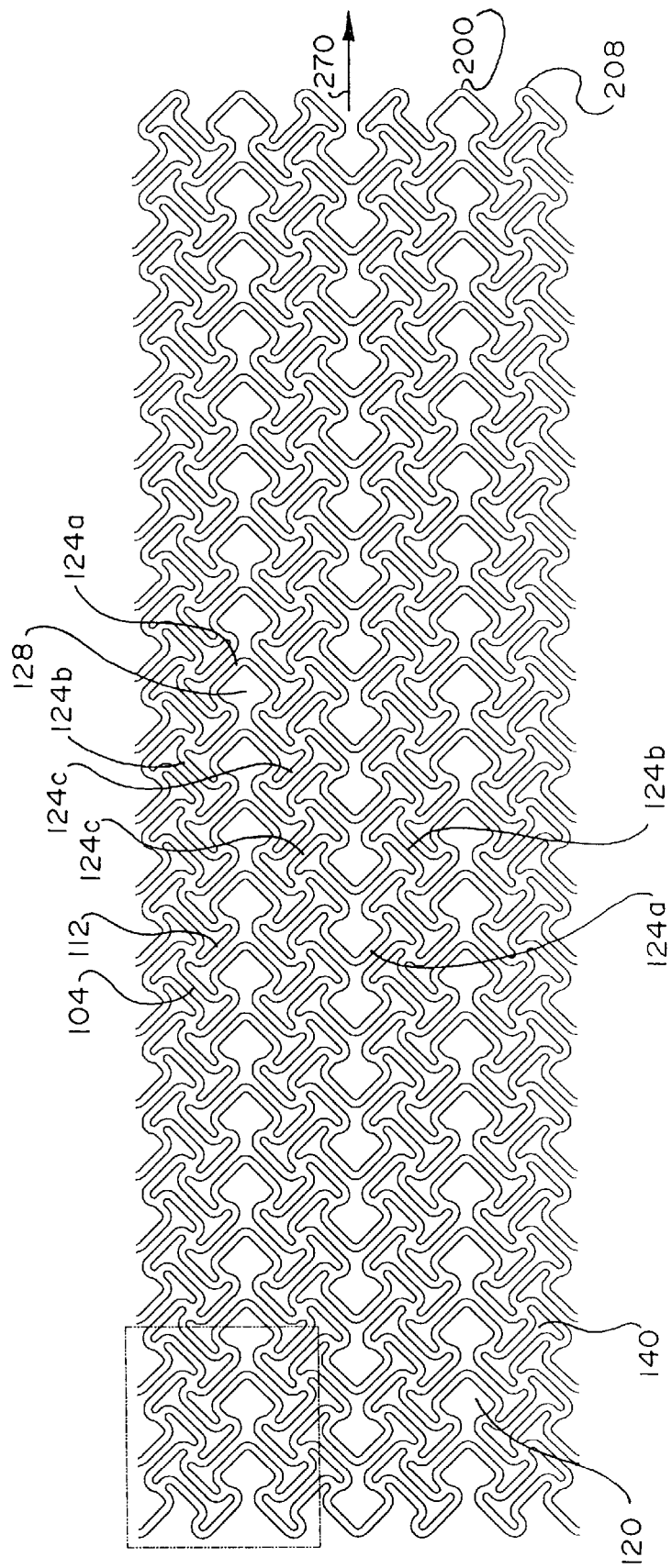
FIG. 18 is a flat plan view showing yet another embodiment of the invention which includes tribonate and bonate structures.

Another embodiment of the stent is shown generally at 200 in FIG. 18. Stent 200 is formed of a plurality of multibonate (tribonate) cells 120 and bonate cells 140. The stent of FIG. 18 is similar to that of FIG. 17 differing in the shape of end portions 124a. End portion 124a is substantially triangular.

In the embodiments of FIGS. 14 and 17, tribonate cell structures include an end portion 124a which is oriented perpendicular to the longitudinal axis of the stent. The invention also contemplates stents in which multibonate cells include an end portion which is parallel to the longitudinal axis of the stent. Such a stent is shown generally at 10 in FIG. 1. End portions 124b are aligned parallel to the longitudinal axis 270 of the stent.

Yet another embodiment of the invention is shown generally at 200 in FIG. 19. Stent 200 is comprised of a series of interconnected, internested quadribonate cells 120 including first quadribonate cells 120a and second quadribonate cells 120b. First and second quadribonate cell 120a,b are differently shaped. End portions 124a of first quadribonate cells 120a also serve as side portions of adjacent second quadribonate cells 120b. First quadribonate cells 120a are joined together by connecting members 154 which also serve as end portions 124b for quadribonate cells 120b. End portions 124a of first quadribonate cell structures 120a are oriented at oblique angles relative to longitudinal axis 270. End portions 124b of second quadribonate cell structures 120b are oriented parallel or perpendicular to longitudinal axis 270 of stent 200. The stent of FIG. 19 is an example of a multibonate stent which consists of at least two different types of multibonate cells of the same order.

Figure 20A:
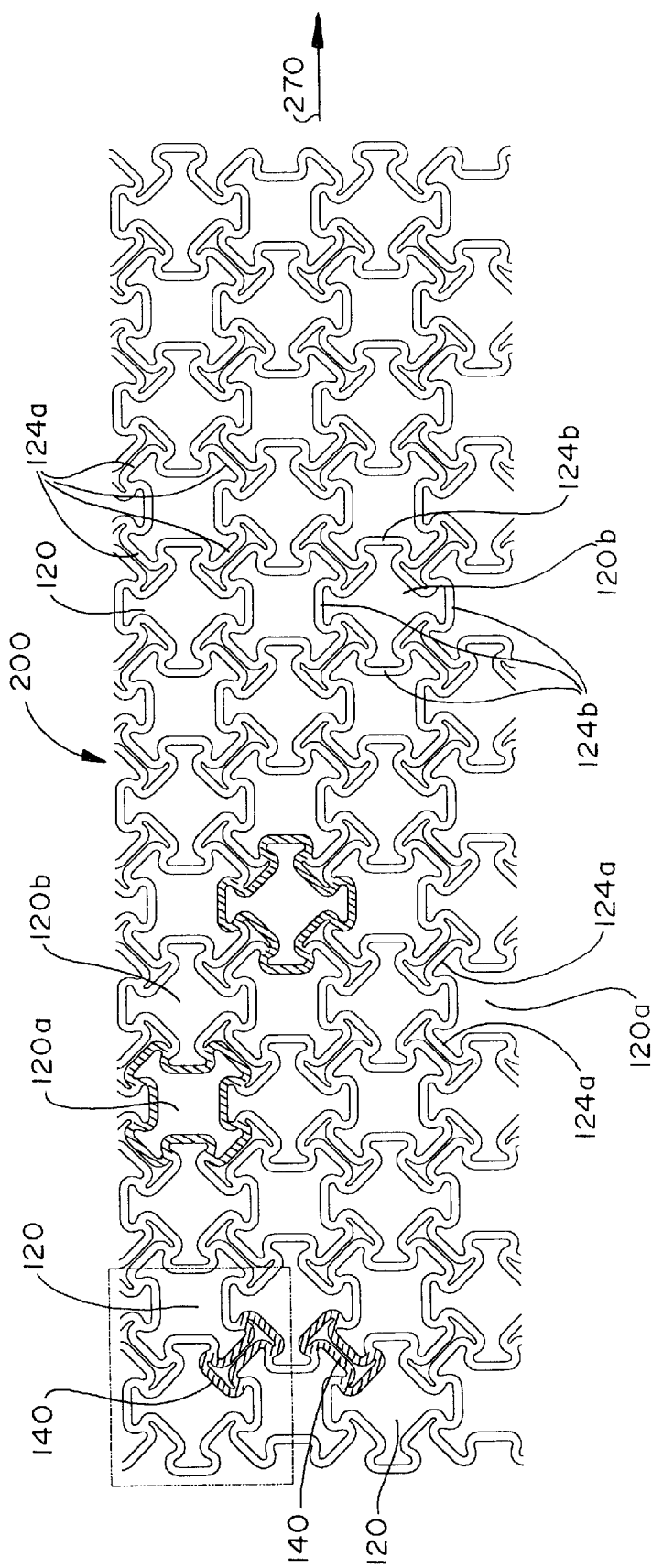
FIG. 20a is a flat plan view showing yet another quadribonate embodiment of the invention.

Another quadribonate stent is shown generally at 200 in FIG. 20a. Stent 200 is formed of a series of interconnected, internested quadribonate cells 120 including first quadribonate 120a and second quadribonate cells 120b. End portions 124a of first quadribonate cell structures 120a are oriented at oblique angles relative to longitudinal axis 270. End portions 124b of second quadribonate cell structures 120b are oriented parallel or perpendicular to longitudinal axis 270 of stent 200. Stent 200 further includes bonate cell structures 140 oriented at oblique angles relative to the longitudinal axis 270 of the stent. The stent of FIG. 20a is an example of a multibonate stent which consists of at least two different types of multibonate cells of the same order and further contains bonate cells.

Figure 20B:
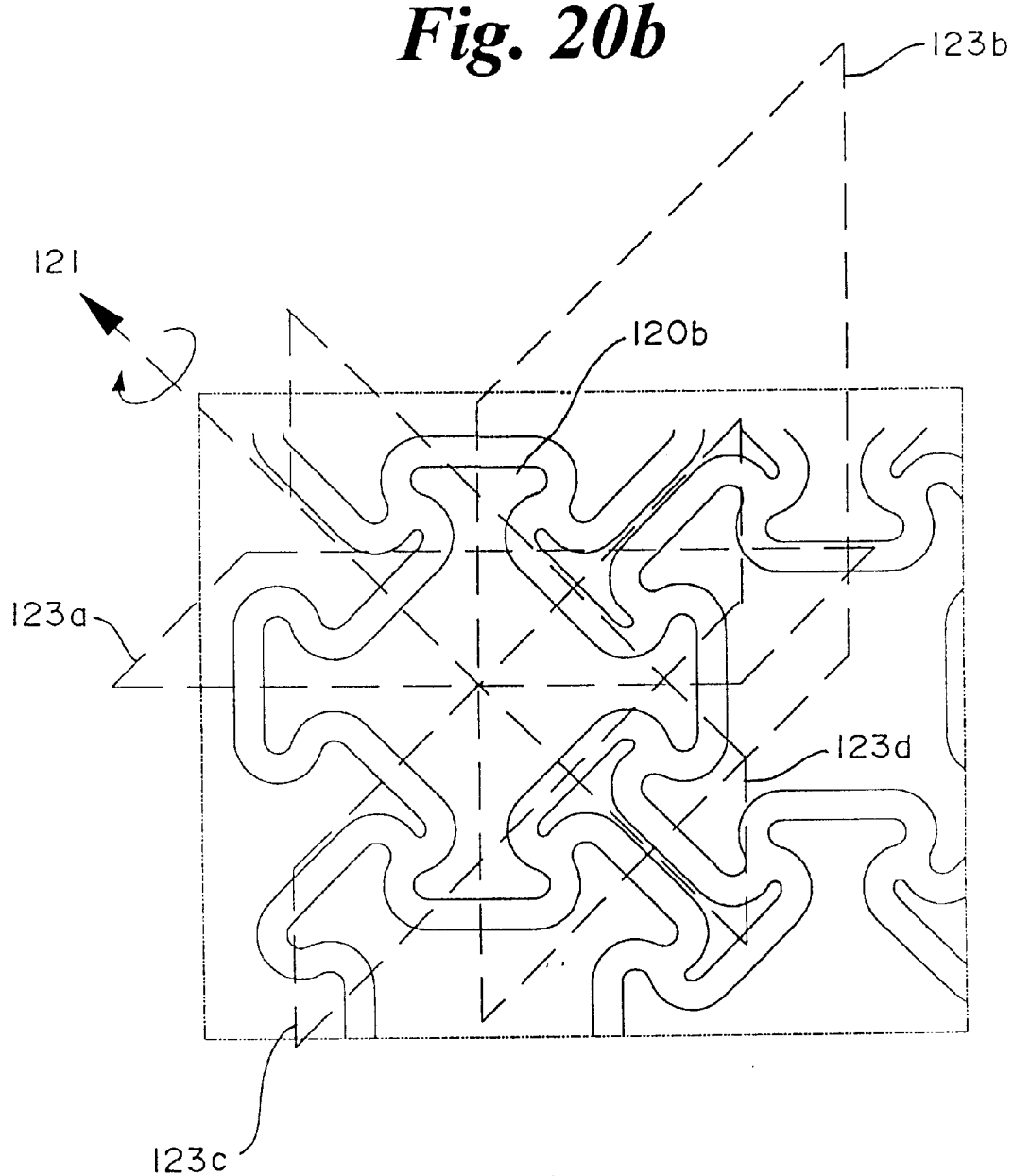
FIG. 20b is an enlarged portion of FIG. 20a showing the various planes of symmetry.

The quadribonate cells of FIGS. 19 and 20 have a four-fold axis of rotational symmetry. FIG. 20b shows this axis 121 for one quadribonate cell 120b of FIG. 20a. The quadribonate cells also are characterized by four planes of reflectional symmetry 123a–d.

Figure 21A:
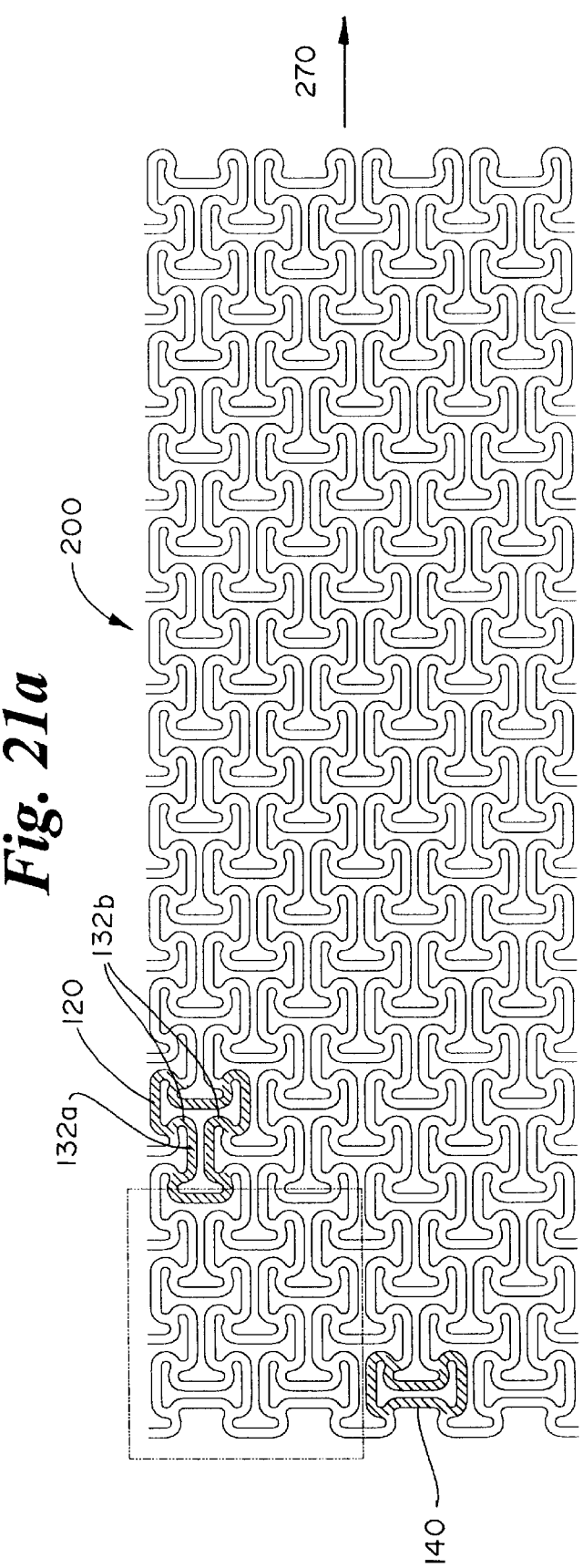
FIG. 21a is a flat plan view showing yet another tribonate embodiment of the invention.
Figure 21B:
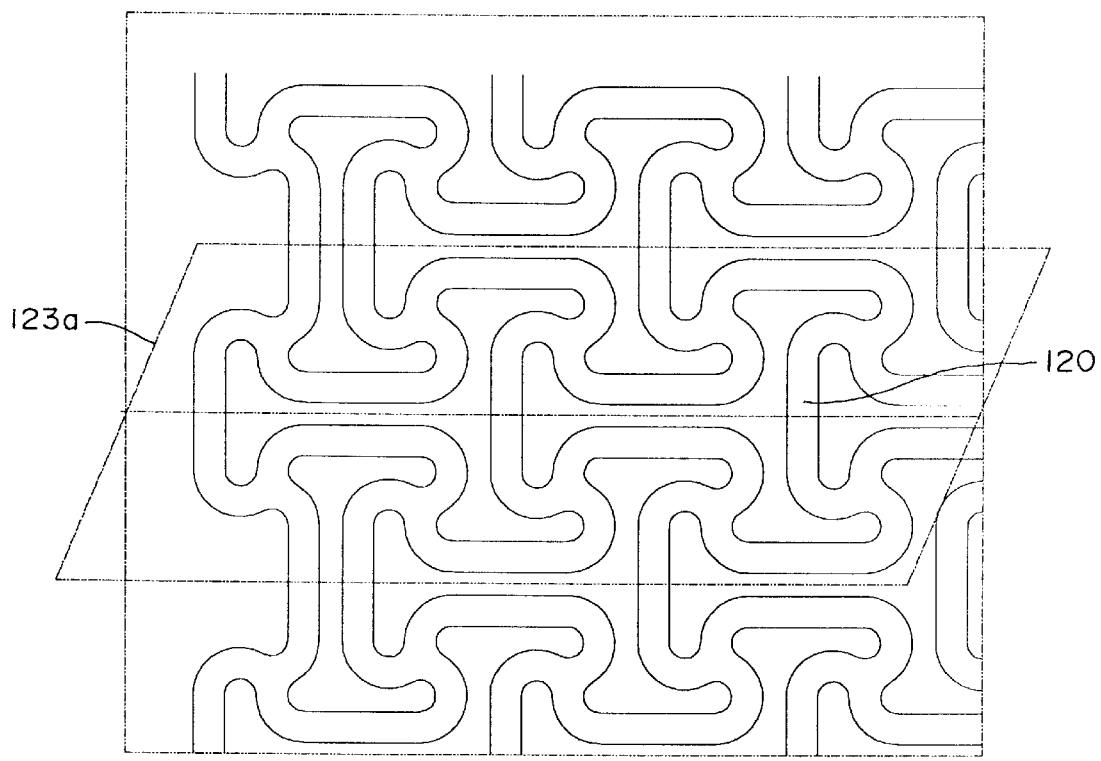
FIG. 21b is an enlarged portion of FIG. 21a showing the various planes of symmetry.

The invention is also directed to a stent, shown generally at 200 in FIG. 21a, which includes elongated tribonate cell structures 120 as well as a row of bonate cell structures 140 at one end of the stent. Tribonate cells 120 include a relatively long, but relatively narrow connecting portion 132a and relatively short and relatively narrow connecting portions 132b. Tribonate cells 120 have a plane of reflectional symmetry 123a as shown in FIG. 21b.

Figure 22A:
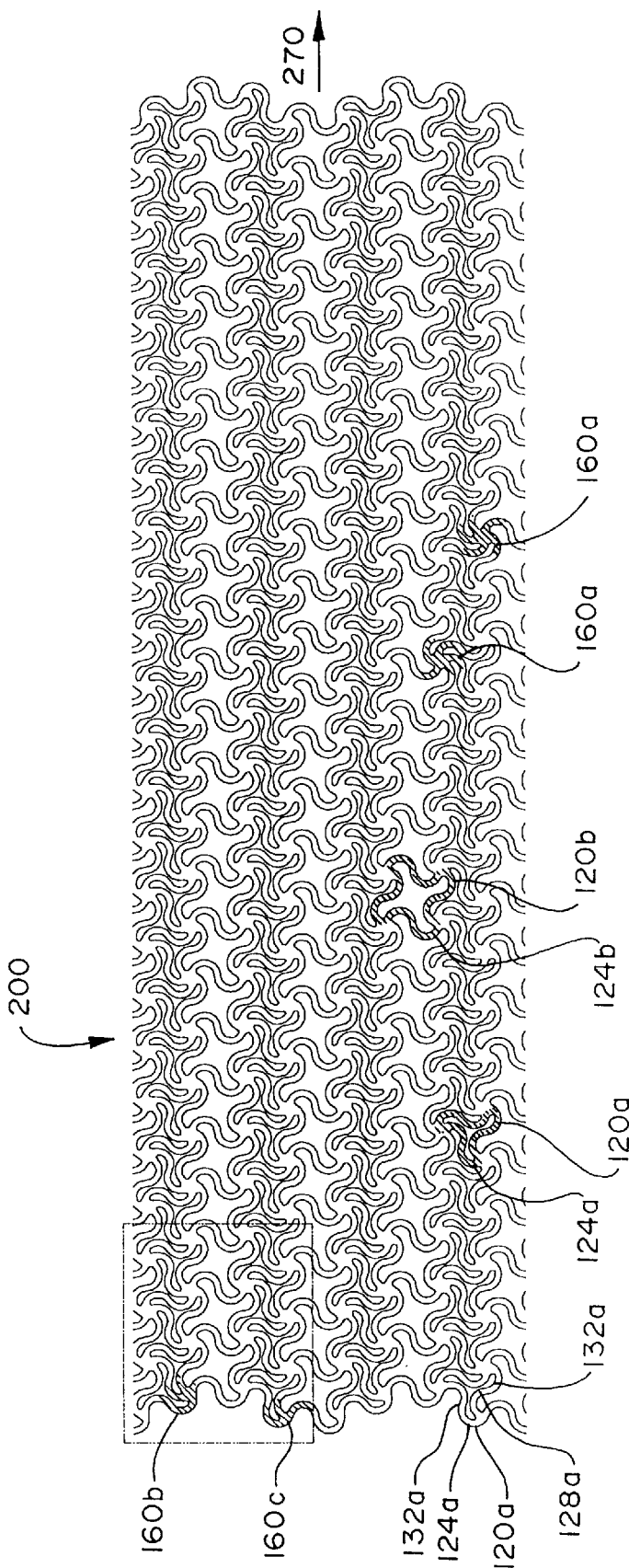
FIG. 22a is a flat plan view showing yet an embodiment of the invention which includes tribonate and quadribonate cells.
Figure 22B:
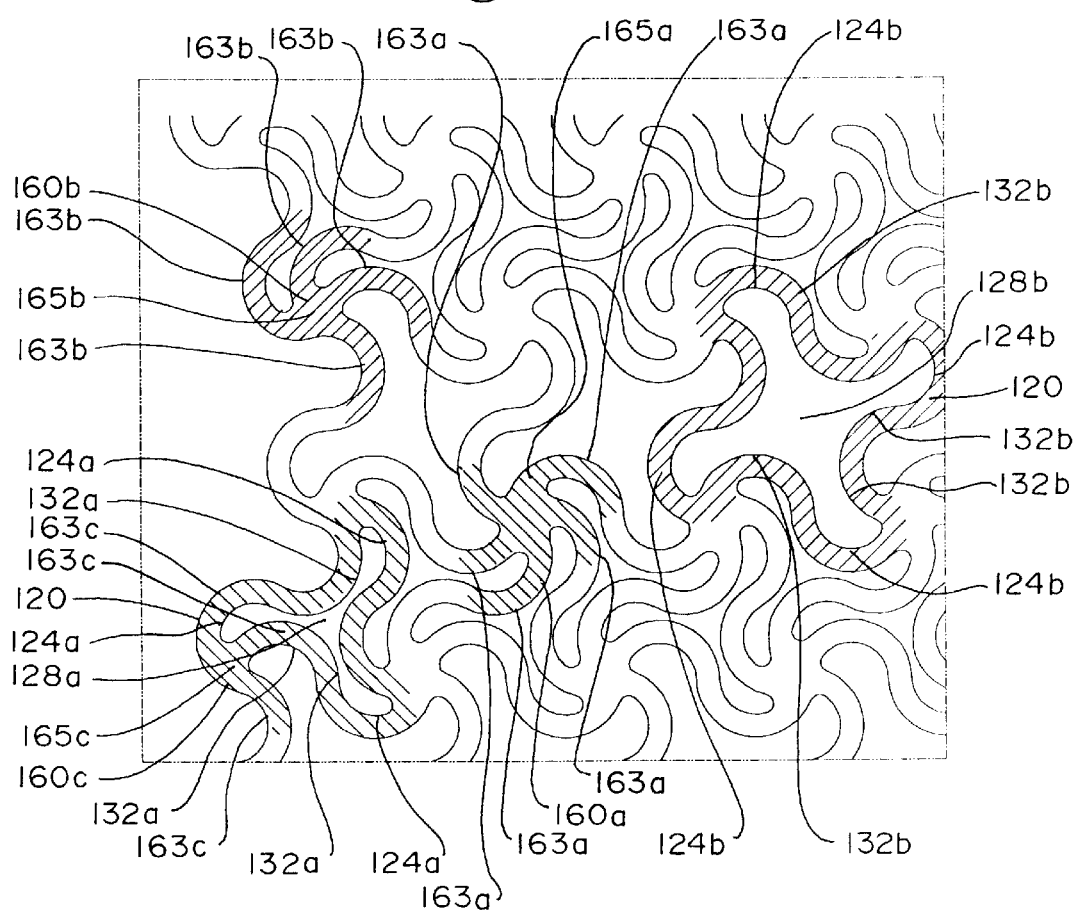

Another embodiment of the inventive stent is shown generally at 200 in FIG. 22a. The pattern of FIG. 22a is magnified in FIG. 22b. Stent 200 is formed of interconnected tribonate cells 120a and interconnected quadribonate cells 120b. Tribonate cells 120a are formed of three relatively wide end portions 124a, each of which is joined to a common portion 128a of the cell via relatively narrow connecting portions 132a. Quadribonate cells 120b are formed of a four relatively wide end portions 124b each of which is joined to a common portion 128b of the cell via relatively narrow connecting portions 132b.

The stent of FIG. 22a also consists of a plurality of interconnected five member spirals 160a, four member spirals 160b and three member spirals 160c. Five member spirals 160a each have five members 163a spiraling about a center portion 165a, four member spirals 160b each have four members 163b spiraling about a center portion 165b and three member spirals 160c each have three members 163c spiraling about a center portion 165c.

Stents having spiral members have also been disclosed in copending, commonly assigned U.S. application Ser. No. 08/846.164, filed Apr. 25, 1997 and incorporated herein in its entirety by reference.

More generally, the invention is directed to stents having multibonate cell structures which include at least one end portion disposed parallel to the longitudinal axis of the stent as well as multibonate cell structures which include at least one end portion disposed perpendicular to the longitudinal axis of the stent.

The invention further contemplates stents which comprise multibonate cell structure in which none of the end portions are perpendicular or parallel to the longitudinal axis of the stent. Such a stent is shown generally at 200 in FIG. 22a. Each of end portions 124a–c are obliquely oriented relative to the longitudinal axis of the stent.

The invention is also directed more generally to stents comprising any order of multibonate structure. A stent comprising sixth order multibonate cell structures is shown generally at 10 in FIG. 9. Hexabonate cell structure 150 consists of six end portions 154 emanating from connector portions. 162 which in turn emanate from a common portion 166. The invention contemplates stents in which adjacent multibonate structures have at least one side in common, as shown in FIG. 9, as well as stent in which adjacent multibonate structures do not have at least one side in common.

The invention is also directed to stents comprising at least one multibonate structure of $n^{th}$ order and at least one bonate structure or multibonate structure of $m^{th}$ order where n and m are integers, n and m are greater than 2 and n≠m. These stents comprise at least one multibonate structure of a desired order and one bonate structure or multibonate structure of a different order.

The stent of FIG. 9 comprises sixth order multibonate structures (hexabonate) 150 as well as third order (tribonate) structures 120. The different order multibonate structures may be interlocking, having parts in common. Tribonate structures 120 in FIG. 9 are interconnected by connecting segments 154 which also serve as end portions of hexabonate cell structures 150. The different order multibonate structures may also be separate from one another and interconnected via connecting members.

The invention also contemplates stents formed of at least two different types of multibonate cell structures of the same order. For example, the two different types of multibonate cells may have different dimensions or different shapes. This is illustrated in FIG. 10. The stent, shown in the flat, includes first tribonate cells 120a and second tribonate cells 120b. The shape of first tribonate cells 120a differs from that of second tribonate cells 120b. FIG. 19 similarly includes two different types of quadribonate cells 120a,b.

The invention is also directed to a stent comprised of at least one cell structure selected from the group consisting of bonate cell structures oriented at an oblique angle relative to the longitudinal axis of the stent, multibonate cell structures and combinations thereof. Desirably, the stent will be composed comprised of a plurality of cell structures selected from the group consisting of bonate cell structures oriented at an oblique angle relative to the longitudinal axis of the stent, multibonate cell structures and combinations thereof. Optionally, the cell structures will be interlocking.

Figure 23:
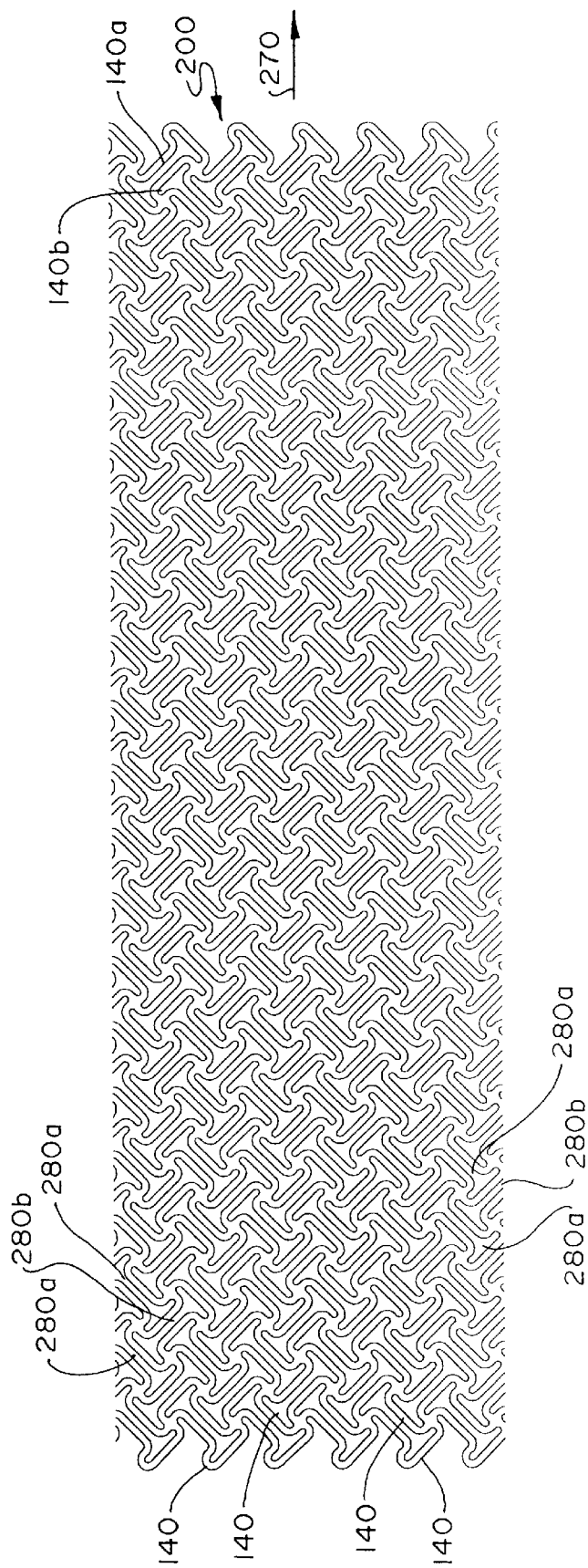
FIG. 23 is a flat plan view showing an embodiment of the invention including obliquely oriented bonate cells.

The invention is further directed to a stent comprising one or more bonate structures oriented at an oblique angle relative to the longitudinal axis of the stent. As shown in the flat in FIG. 23, stent 200 consists of interconnected bonate cell structures 140. The stent includes first bonate cell structures 140a which are oriented at a first oblique angle relative to the longitudinal axis of the stent 270 and second bonate cell structures 140b which are oriented at a second oblique angle relative to the longitudinal axis of the stent. The second oblique angle is equal but opposite to the first oblique angle. The stent of FIG. 23 consists of alternating rows 280a and 280b of first bonate cell structures 140a and second bonate cell structures 140b, respectively, disposed about the circumference of the stent.

All of the configurations shown in the Figures may be utilized uniformly throughout a stent or they may be mixed as a means of tailoring a variety of different characteristics throughout various regions of a stent. Other cell configurations may also be used in the practice of the invention.

It is understood that the invention contemplates substituting straight sections of the cell structure for curved structures and vice versa as long as the multibonate structure of the cells is maintained.

It is also understood that the term stent, as used in this application, is directed to stents, stent-grafts, grafts and other endoluminal and intraluminal prostheses. For example, the configurations disclosed herein may be used as a framework for grafts.

It will be also appreciated that, while the specific shapes depicted in the figures hereof contain many functional features, those functional features can all readily be obtained in other embodiments which have an overall appearance which is quite different. Therefore, the article of the figures is considered to have a novel and non-obvious ornamental appearance independent of the functional features described herein.

While this invention may be embodied in many different forms, there are described in detail herein specific preferred embodiments of the invention. This description is an exemplification of the principles of the invention and is not intended to limit the invention to the particular embodiments illustrated.

Those familiar with the art may recognize other equivalents to the specific embodiments described herein which equivalents are also intended to be encompassed by the claims attached hereto.

What is claimed is as follows:

1. A stent of generally cylindrical shape having a longitudinal axis, the stent comprised of at least one multibonate cell structure, the multibonate cell structure having at least three end portions, at least two of the end portions defining openings axis of which are non-parallel to the longitudinal axis of the stent each defining an opening along a longitudinal axis thereof.

2. The stent of claim 1 comprised of a plurality of interconnected multibonate cell structures.

3. The stent of claim 2 wherein the multibonate cell structures are regularly arranged.

4. The stent of claim 2 wherein at least one of the multibonate cell structures is tribonate, having:
   a common portion;
   a first connecting portion extending from the common portion;
   a first end portion extending from the first connecting portion;
   a second connecting portion extending from the common portion;
   a second end portion extending from the second connecting portion;
   a third connecting portion extending from the common portion; and
   a third end portion extending from the third connecting portion.

5. The stent of claim 4 wherein the multibonate structures are arranged in interconnected longitudinal rows.

6. The stent of claim 5 wherein a plurality of the multibonate cell structures are tribonate.

7. The stent of claim 6 wherein adjacent rows of multibonate structures have connecting members extending therebetween.

8. The stent of claim 6 wherein adjacent multibonate structures within a row are interlocking.

9. The stent of claim 6 wherein adjacent rows of multibonate structures have connecting members extending therebetween, the connecting members being bonate cell structures.

10. The stent of claim 9 wherein each bonate cell structure is disposed at an oblique angle relative to the longitudinal axis.

11. The stent of claim 10 wherein the bonate cell structures are arranged in longitudinal rows,
    all of the bonate cells within a row disposed at the same oblique angle,
    bonate cell structures in adjacent rows of bonate structures oppositely disposed about a line parallel to the longitudinal axis of the stent extending between the adjacent rows of bonate structures and equidistant from the adjacent rows of bonate structures.

12. The stent of claim 6 wherein all of the multibonate structures are tribonate and tribonate structures in adjacent rows of multibonate structures are rotated 180° relative to one another.

13. The stent of claim 6 wherein all of the multibonate structures are tribonate and tribonate structures in adjacent rows of multibonate structures are identically oriented relative to the longitudinal axis of the stent.

14. The stent of claim 6 wherein each multibonate structure is defined by a plurality of interconnected side portions and at least some of the multibonate structures have a side portion in common.

15. The stent of claim 14 wherein the multibonate structures are tribonate.

16. The stent of claim 15 wherein the multibonate structures are disposed in longitudinal rows and adjacent multibonate structures in adjacent rows of multibonate structures share at least one side portion in common.

17. The stent of claim 6 wherein the tribonate structure has a threefold rotational axis of symmetry in the flat.

18. The stent of claim 6 wherein the tribonate structure has a single plane of reflectional symmetry $\sigma_v$.

19. The stent of claim 6 wherein the second and third connecting portions are substantially the same length.

20. The stent of claim 6 wherein all three connecting portions are substantially the same length.

21. The stent of claim 6 where at least one of the end portions is substantially triangular in shape.

22. The stent of claim 21 wherein the substantially triangular end portion has convex sides.

23. The stent of claim 6 wherein at least two of the end portions are substantially rectangular in shape.

24. The stent of claim 23 wherein the substantially rectangular end portions are formed of
    a first side portion extending from the connecting portion;
    a second side portion opposite the first side portion and extending from the connecting portion; and
    an end base portion extending between the first and second side portions, wherein the base portion is substantially linear.

25. The stent of claim 23 wherein the substantially rectangular end portions are formed of
    a first side portion extending from the connecting portion;
    a second side portion opposite the first side portion and extending from the connecting portion; and
    an end base portion extending between the first and second side portions, wherein the base portion is a convex curve.

26. The stent of claim 6 wherein at least some of the multibonate structures are hexabonate structures.

27. The stent of claim 26 wherein adjacent hexabonate structures have at least one side in common.

28. The stent of claim 26 further comprising tribonate structures.

29. The stent of claim 28 wherein the hexabonate and tribonate structures are interlocking.

30. The stent of claim 8 comprising at least one multibonate structure of $n^{th}$ order and at least one multibonate structure of $m^{th}$ order
    where n and m are integers greater than 2; and
    n≠m.

31. The stent of claim 6 wherein all of the multibonate cell structures are of the same tribonate cell structure.

32. The stent of claim 6 comprising interconnected quadribonate cell structures.

33. A stent of generally cylindrical shape having a longitudinal axis, the stent comprised of a plurality of multibonate cell structures, wherein all of the multibonate cell structures are tribonate, each tribonate structure having
    a common portion;
    a first connecting portion extending from the common portion;

a first end portion extending from the first connecting portion;

a second connecting portion extending from the common portion;

a second end portion extending from the second connecting portion;

a third connecting portion extending from the common portion; and a third end portion extending from the third connecting portion wherein at least two of the end portions defining openings which are non-parallel to the longitudinal axis of the stent.

34. The stent of claim 33 wherein the multibonate structures are arranged in interconnected longitudinal rows.

* * * * *